United States Patent
LoVetri et al.

(10) Patent No.: US 11,090,366 B2
(45) Date of Patent: *Aug. 17, 2021

(54) COMPOSITIONS AND METHODS FOR REDUCING ORAL BIOFILM

(75) Inventors: Karen LoVetri, Winnipeg (CA); Srinivasa Madhyastha, Winnipeg (CA); Nandadeva Yakandawala, Winnipeg (CA); Purushottam V. Gawande, Winnipeg (CA); Gord Froehlich, Selkirk (CA)

(73) Assignee: Kane Biotech Inc., Winnipeg (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,308

(22) PCT Filed: Jun. 27, 2012

(86) PCT No.: PCT/CA2012/050432
§ 371 (c)(1),
(2), (4) Date: Oct. 7, 2014

(87) PCT Pub. No.: WO2013/063695
PCT Pub. Date: May 10, 2013

(65) Prior Publication Data
US 2015/0087582 A1    Mar. 26, 2015

Related U.S. Application Data

(60) Provisional application No. 61/654,490, filed on Jun. 1, 2012, provisional application No. 61/641,503, filed on May 2, 2012, provisional application No. 61/553,506, filed on Oct. 31, 2011.

(51) Int. Cl.
| | | |
|---|---|---|
| *A61K 38/40* | (2006.01) | |
| *A61K 31/198* | (2006.01) | |
| *A61K 31/194* | (2006.01) | |
| *A61K 45/06* | (2006.01) | |
| *A61K 8/365* | (2006.01) | |
| *A61K 9/127* | (2006.01) | |
| *A61K 8/44* | (2006.01) | |
| *A61K 8/64* | (2006.01) | |
| *A61Q 17/00* | (2006.01) | |
| *A61K 31/315* | (2006.01) | |
| *A61K 47/60* | (2017.01) | |
| *A61Q 11/00* | (2006.01) | |
| *A61K 9/51* | (2006.01) | |
| *A61K 9/00* | (2006.01) | |

(52) U.S. Cl.
CPC .............. *A61K 38/40* (2013.01); *A61K 8/365* (2013.01); *A61K 8/44* (2013.01); *A61K 8/64* (2013.01); *A61K 9/0063* (2013.01); *A61K 9/127* (2013.01); *A61K 9/5153* (2013.01); *A61K 31/194* (2013.01); *A61K 31/198* (2013.01); *A61K 31/315* (2013.01); *A61K 45/06* (2013.01); *A61K 47/60* (2017.08); *A61Q 11/00* (2013.01); *A61Q 17/005* (2013.01); *A61K 2800/51* (2013.01)

(58) Field of Classification Search
CPC .... A61K 31/194; A61K 31/198; A61K 38/40; A61K 45/06; A61K 2300/00; A61K 31/315; A61K 2800/51; A61K 47/48215; A61K 8/365; A61K 8/44; A61K 8/64; A61K 9/0063; A61K 9/127; A61K 9/5153; A61K 33/30; A61K 2800/70; A61K 8/27; A61P 31/04; A61P 1/02; A61P 27/02; A61P 31/00; A61Q 17/005; A61Q 11/00; A61Q 3/00
See application file for complete search history.

(56) References Cited

U.S. PATENT DOCUMENTS

| | | |
|---|---|---|
| 3,887,712 A | 6/1975 | Lover et al. |
| 4,060,600 A | 11/1977 | Vit |
| 4,119,711 A | 10/1978 | Hernestam et al. |

(Continued)

FOREIGN PATENT DOCUMENTS

| | | | | |
|---|---|---|---|---|
| CN | 101756794 A | * | 6/2010 | ............. A61K 38/00 |
| WO | WO 9418939 A1 | * | 9/1994 | ............... A61K 7/22 |

(Continued)

OTHER PUBLICATIONS

N. Yakandawala, Effect of ovotransferrin, protamine sulfate and EDTA combination on biofilm formation by catheter-associated bacteria, Journal of Applied Microbiology 102 (2007) 722-727.*
Steven Opal, Clinical Gram-positive sepsis: Does it fundamentally differ from Gram-negative bacterial sepsis?, Critical care Medicine, Issue: vol. 27(8), 1999, pp. 1-14.*
National Institute of Dental and Craniofacial Research, Chapter 3: Diseases and Disorders, www.nidcr.nih.gov/DataStatistics/SurgeonGeneral/sgr/chap3, 2008.*

(Continued)

*Primary Examiner* — James H Alstrum-Acevedo
*Assistant Examiner* — Erinne R Dabkowski
(74) *Attorney, Agent, or Firm* — Ridout & Maybee LLP

(57) ABSTRACT

Compositions comprising iron-sequestering glycoproteins, chelating agents, stabilizing agents, binding agents, surfactants, fluorides, antimicrobials and a pH adjuster or buffer for the prevention and treatment of oral cavity diseases caused by dental plaque/biofilm, such as dental caries, gingivitis and periodontitis, through anti-infective properties are disclosed. The anti-infective properties of a composition include reduction or killing of anaerobic/aerobic/facultative gram-negative and gram-positive oral bacteria occurring in polymicrobial dental biofilms. The composition may be in the form of wash, rinse, soak, paste, gel, spray, or other suitable form. Additionally, the invention offers an efficient method of delivering the formulated composition containing a PEGylated or fluorinated iron-sequestering glycoprotein and one or two chelating agents or chelating agents alone using either a liposomal or a nanoparticle delivery system.

11 Claims, 10 Drawing Sheets

(56) References Cited

U.S. PATENT DOCUMENTS

| | | | |
|---|---|---|---|
| 4,160,821 A | | 7/1979 | Sipos |
| 4,178,363 A | | 12/1979 | Miller, Jr. |
| 4,610,871 A | | 9/1986 | Lynch |
| 4,999,184 A | | 3/1991 | Parran, Jr. et al. |
| 5,104,644 A | * | 4/1992 | Douglas ............... 424/53 |
| 5,174,990 A | * | 12/1992 | Douglas ........ A61K 8/22 424/49 |
| 5,304,540 A | * | 4/1994 | Blackburn ......... A01N 37/46 514/2.8 |
| 5,310,546 A | * | 5/1994 | Douglas ............... 424/53 |
| 5,932,469 A | | 8/1999 | Hillman |
| 6,218,362 B1 | | 4/2001 | Lavoie et al. |
| 6,294,186 B1 | | 9/2001 | Beerse |
| 6,342,385 B1 | | 1/2002 | Qi et al. |
| 6,391,285 B1 | | 5/2002 | Hillman |
| 6,475,771 B1 | | 11/2002 | Hillman |
| 6,589,562 B1 | | 7/2003 | Shefer et al. |
| 6,696,047 B2 | | 2/2004 | Scott et al. |
| 6,699,839 B1 | | 3/2004 | Lavoie et al. |
| 6,699,970 B2 | | 3/2004 | Qi et al. |
| 7,597,895 B2 | | 10/2009 | Huang et al. |
| 2005/0101605 A1 | * | 5/2005 | Ahmed ............ A61K 9/0095 514/251 |
| 2005/0170013 A1 | | 8/2005 | Douglas |
| 2006/0140876 A1 | * | 6/2006 | Balasch Risueno ..... A61K 8/27 424/49 |
| 2009/0221483 A1 | | 9/2009 | Melgarejo |
| 2010/0106103 A1 | | 4/2010 | Ziebol |

FOREIGN PATENT DOCUMENTS

| | | | | |
|---|---|---|---|---|
| WO | WO 2006068753 A1 | * | 6/2006 | ........... A61K 8/0216 |
| WO | WO 2006089139 A2 | * | 8/2006 | ............. A61F 13/38 |

OTHER PUBLICATIONS

The On-line Medical Dictionary, Definition of Analogue, accessed on Jul. 7, 2005.*

English Translation of CN101756794 A, description and claims, accessed on Nov. 23, 2015.*

Eun-Kyoung Choi, Potentiation of Bacterial Killing Activity of Zinc Chloride by Pyrrolidine Dithiocarbamate, The Journal of Microbiology (2010) vol. 48, No. 1, pp. 40-43 Copyright © 2010, The Microbiological Society of Korea.*

H. Babich A, Toxicity of Zinc to Fungi, Bacteria, and Coliphages: Influence of Chloride Ions, Applied and Environmental Microbiology, Dec. 1978, p. 906-914.*

* cited by examiner

COMPOSITIONS AND METHODS FOR REDUCING ORAL BIOFILM

CROSS-REFERENCE TO RELATED APPLICATIONS

This application claims the benefit of and priority to U.S. Patent Application Nos. 61/553,506 filed Oct. 31, 2011; 61/641,503 filed May 2, 2012 and 61/654,490 filed Jun. 1, 2012 respectively.

The content of the above patent applications is hereby expressly incorporated by reference into the detailed description hereof.

FIELD OF THE INVENTION

This invention relates to methods of using compositions for preventing and treating oral cavity diseases. It further relates to methods of formulating the compositions comprising iron-sequestering glycoproteins, chelating agents and pharmaceutically acceptable excipients, by applying them to oral cavity. More particularly, the invention relates to an efficient method of delivering a pharmaceutically acceptable formulation containing a PEGylated or fluorinated iron-sequestering glycoprotein and one or two chelating agents using either a liposomal or a nanoparticle delivery system.

BACKGROUND OF THE INVENTION

Dental plaque is a diverse community of microorganisms found on the tooth surface embedded in an extracellular matrix of host and microbial polymers. An important environmental effect of the plaque is the development of a low-oxygen environment that promotes the colonization and growth of anaerobic bacteria. Microorganisms in the plaque synthesize a slime matrix or glycocalyx (biofilm) from abundant polysaccharides, glycoproteins, and dietary sugars (e.g., sucrose) present in the oral environment. Eventually, the plaque becomes a characteristic dental biofilm with a highly structured, matrix-embedded, diverse microbial population altering gene expression severely.

Dental plaque is a precursor of calculus. Dental calculus, or tartar, refers to a build-up of hardened (mineralized) plaque on the teeth, formed by the presence of saliva, debris, and minerals. Mature calculus consists of an inorganic portion which is largely calcium phosphate arranged in a hydroxyapatite crystal lattice structure similar to bone, enamel, and dentine. An organic portion is also present and consists of desquamated epithelial cells, leukocytes, salivary sediment, food debris, and various types of microorganisms. Its rough surface provides an ideal medium for bacterial growth, threatening the health of the gums and absorbing unaesthetic stains far more easily than natural teeth.

Dental plaque can occur above (supragingival) and below (subgingival) the gumline. Supragingival dental plaque forms on teeth within hours after they are cleaned. In the presence of a diet rich in sucrose, shifts occur in the supragingival plaque to more of an acidogenic plaque, with dental caries as an outcome. Plaques that form on subgingival tooth surfaces and coat the epithelium lining of the gingival crevice lead to the development of periodontal infections (i.e., gingivitis and periodontitis).

Dental caries is characterized by dissolution of the mineral portion of the tooth, which can result in pain and loss of viability of the tooth, necessitating costly repair or extraction of the tooth. Dental caries affects 50% of children aged 5-9 years, 67% of adolescents aged 12-17 years, and 94% of adults aged 18 years in the US (*Morbidity and Mortality Weekly Reports* 51: 144-147, 2002). Clean teeth will not decay; however, even with vigorous cleaning it is difficult to keep teeth sufficiently clean. Various methods have been developed to prevent or alleviate dental caries including, for example, the addition of sodium fluoride, sodium silicofluoride or hydrofluosilicic acid to drinking water, and sodium fluoride or tin fluoride to topical preparations, including dentifrices and mouth rinses. The prevention of caries by coating teeth with polymeric materials or sealants has been used; however, these techniques are costly, can require etching of the teeth with phosphoric acid and can be effective only in young children who have not yet developed caries. Antibacterial agents, including antibiotics, have also been proposed as a treatment for dental caries.

Oral streptococci and *Actinomyces* spp. are the first to appear on the surface of the teeth. Streptococci account for approximately 20% of the salivary bacteria, which include *Streptococcus* spp. such as *Streptococcus mutans, Streptococcus sobrinus, Streptococcus sanguis, Streptococcus gordonii, Streptococcus oralis* and *Streptococcus mitis*. Although four streptococci, *S. mutans, S. sobrinus, S. sanguis* and *S. oralis* are directly involved in the initiation of dental caries, *S. mutans* is considered to be a principal etiological agent of caries (Devulapalle et al., *Carbohydr. Res.* 339:1029-1034, 2004). As *S. mutans* has evolved to depend on a biofilm lifestyle for survival and persistence in the oral cavity combined with its role as an opportunistic pathogen, it has become the best-studied example of a biofilm-forming, disease-causing *Streptococcus* (Burne, R. A., *J. Dent. Res.* 77: 445-452, 1998).

Bacteria in dental plaque are the major cause of gingivitis, chronic and aggressive periodontitis, and necrotizing periodontal diseases. Gingiva (gums) are part of the soft tissue lining in the mouth surrounding the teeth. Gingivitis is an inflammation of the gums that often appears as swollen, red, or bleeding gums. It is generally believed that plaque-forming bacteria that live in the mouth and on tooth surfaces are a cause of gingivitis and certain substances released by the bacteria cause the gum inflammation. Therefore, reducing plaque bacteria can decrease inflammatory substances and effect a reduction in gingivitis. Studies have shown that gingivitis will develop within 10-21 days without oral hygiene practices allowing for the accumulation of plaque. Approximately 80% of U.S. adults have a case of gum/periodontal disease. Gingivitis is preventable by routine oral care, but if untreated may lead to severe gum disease known as periodontitis. Periodontitis is characterized by a group of infections which destroy supporting tissue and bone by plaque-induced inflammation. Chronic periodontitis is the most common form affecting approximately 20% of the adult U.S. population. Symptoms include the formation of deep periodontal pockets, gingival recession, increased tooth mobility, and loss of bone as detected by radiographs. If left untreated, periodontitis can lead to tooth loss.

*Aggregatibacter actinomycetemcomitans* (Aa) is the principal etiologic agent of early-onset periodontitis including localized and generalized prepubertal periodontitis, localized and generalized juvenile periodontitis, and rapidly progressive or refractory adult periodontitis. Tooth loss is the ultimate detrimental effect of destructive periodontal disease. A national survey of the United States revealed a prevalence of localized juvenile periodontitis of 0.53% and of generalized juvenile periodontitis of 0.13%. Loe & Brown, *J. Periodontol.* 62:608-616 (1991). Findings from a number of studies corroborate the conclusion that early-onset disease is similar in other industrialized countries and is more frequent in developing countries. Loe & Brown, *J. Periodontol.* 62:608-616 (1991). In addition, certain types of adult periodontitis, which in general are very common conditions affecting over half the adult population, are likely to be caused by a select group of microorganisms indigenous to the oral cavity.

A variety of chemical and biological agents have also been suggested to retard calculus formation or to remove calculus after it is formed. Pyrophosphate salts and other chemical agents are known to have the ability to retard calculus formation. For example, in U.S. Pat. Nos. 4,999, 184 and 4,610,871, the use of monoalkyl or dialkyl ethers of dianhydrohexitols to inhibit the formation of plaque and calculus on teeth is described. U.S. Pat. No. 4,178,363 describes the use of n-undecylenic fatty acid or a calcium or zinc salt thereof for reducing dental plaque and infections of the teeth and gums. U.S. Pat. No. 4,119,711 describes spiro 1-(hydroxyalkyl)-piperidino derivatives which have efficacy in reducing the formation of plaque.

Additionally, U.S. Pat. No. 3,887,712 discloses that alexidine dihydrofluoride is useful in the treatment of dental plaque, calculus, gingivitis and related periodontal diseases. U.S. Pat. No. 4,160,821 discloses that a glycerin solution of zinc chloride or other acceptable zinc salts provides effective therapy for gingivitis when applied to the gingival and teeth. U.S. Pat. No. 4,060,600 teaches a method of treating teeth in dentistry, for the prevention of calculus, removal of caries, and dissolution of plaque, comprising applying an aqueous solution containing a hypochlorite of an alkali and/or alkaline earth metal, and an amino compound capable of forming water-soluble non-mucous irritating N-chloro and/or N-dichloro derivatives thereof to the teeth.

Current preventative measures for reducing gingivitis include good oral hygiene such as the use of antiplaque or antitartar toothpastes and the use of mouth rinses and floss. These products loosen and remove deposits/bacteria from the teeth and clean the teeth. For treatment of gingivitis, antibacterial mouthwash can be used in addition to frequent, careful, tooth brushing and flossing. This type of mouthwash typically comprises hexetidine, chlorhexidine digluconate, or cetylpyridinium chloride. The goal for this type of product is to reduce the amount or effects of microorganisms and bacteria.

Tetracycline has been widely used in the treatment of early-onset periodontitis. There remains a concern, however, of strains developing resistance to tetracycline as well as the possibility of overgrowth of other pathogenic microorganisms. Given the incidence of periodontal diseases, safe preventative and treatment strategies are needed in the art. Control of periodontal disease is also very important in light of recent attention to the possible role of periodontal infections as risk factors for systemic disease (e.g., coronary heart disease). Therefore, methods of treatment and prevention of early-onset periodontitis, localized and generalized juvenile periodontitis, and rapidly progressive or refractory adult periodontitis are needed in the art.

The delivery of oral care compounds through the formation of multicomponent particles, wherein one of the components is a moisture sensitive barrier layer which surrounds nanoparticles composed of wax, active ingredient, and cationic lipids, is disclosed in U.S. Pat. No. 6,589,562. U.S. Pat. No. 6,696,047 discloses stabilizing sodium chlorite in a variety of oral care compositions, such as toothpastes or oral rinse products. The stabilization of highly reactive sodium chlorite is achieved by ensuring that the pH of the final composition is at least 10 or greater. This is a significant limitation for oral care compositions which may include pH sensitive components, such as polyphosphates.

In general, chemical and biological agents have some disadvantages, such as discoloration of teeth or tongue, desquamation and soreness of oral mucosa, objectionable taste, toxicity, and may also cause an imbalance of the oral flora. In addition, almost all the active chemical and biological agents in the marketed oral care products have antibacterial/antimicrobial activity and/or biofilm inhibition activity. In other words, these agents are ineffective against bacteria in a pre-existing dental biofilm (dental plaque). Thus, there is a need for developing biologically safe and effective oral care products containing active ingredients with both the antimicrobial and biofilm inhibition as well as disruption activity.

SUMMARY OF THE INVENTION

A need remains in the art for an efficient delivery system to effectively incorporate oral care compounds into an oral care composition. One type of delivery system that can achieve these attributes in an oral care composition is the adsorbent nanoparticle or microparticle delivery systems.

The instant invention provides compositions and methods for the maintenance of oral health by preventing and/or treating oral cavity diseases such as dental caries, gingivitis, periodontitis, dental caries, and oral bacterial infections or diseases.

One embodiment of the invention provides a composition comprising: (a) an iron-sequestering glycoprotein; and (b) one or two chelating agents.

In another embodiment, a composition of the invention comprises: (a) a small amount of at least one iron-sequestering glycoprotein, (b) a small amount of at least one chelating agent, wherein the amount of each of components (a) and (b) is sufficient to form an effective anti-infective composition against bacterial infections in oral cavity.

In yet another embodiment, a composition of the invention comprises: (a) a small amount of at least one iron-sequestering glycoprotein, (b) a small amount of at least one chelating agent, and (c) a pharmaceutically acceptable excipients.

Still another embodiment of the invention provides an anti-infective composition comprising an iron-sequestering glycoprotein and one or two chelating agents that are effective against bacteria and fungi causing oral diseases such as dental caries, gingivitis and periodontitis. The composition is effective against oral disease-associated bacteria.

A further embodiment of the invention provides an anti-infective composition comprising an iron-sequestering glycoprotein and one are two chelating agents that are effective against veterinary oral disease-associated bacteria.

In an embodiment, the iron-sequestering glycoprotein is between about 50 mg/L and about 500 mg/L of the composition. The chelating agent is between about 400 mg/L and about 4,000 mg/L of the composition.

The iron-sequestering glycoprotein may be selected from the group consisting of holo- and apo-ovotransferrins, holo- or apo-lactoferrin and serotransferrins. The chelating agents may be selected from the group consisting of EDTA, EGTA, DTPA, EDDHA, IDA, CDTA, HEDTA, HEIDA, NTA, sodium citrate, potassium citrate and zinc citrate.

In another embodiment, the iron-sequestering agent is apo-ovotransferrin and the chelating agent is disodium EDTA. The apo-ovotransferrin may be present at about 1 mg/ml and the disodium EDTA may be present at about 2 mg/ml.

In yet another embodiment, the iron-sequestering agent is lactoferrin and the chelating agent is disodium EDTA. The lactoferrin may be present at about 0.05 mg/ml and the disodium EDTA may be present at about 2 mg/ml.

In a further embodiment, the iron-sequestering agent is lactoferrin and the chelating agents are disodium EDTA and sodium citrate. The lactoferrin may be present at about 0.05 mg/ml and the disodium EDTA and sodium citrate may be present at about 2 mg/ml and 3 mg/ml, respectively.

Still another embodiment of the invention provides an antibiofilm-antimicrobial oral composition comprising disodium EDTA and sodium citrate. The disodium EDTA may be present at about 1 mg/ml, preferably from about 0.5 mg/ml to about 0.25 mg/ml, and most preferably from about 0.025 mg/ml to about 0.010 mg/ml. The sodium citrate may be present at about 3 mg/ml, preferably from about 2 mg/ml to about 1 mg/ml.

The composition may further comprise one or more ingredients selected from the group consisting of: water, citrate buffer, stabilizing agent, a flavoring agent, vitamins, minerals (zinc citrate, zinc lactate, zinc gluconate, zinc chloride, etc.), herbals, a surfactant, an antimicrobial peptide, an antimicrobial and a pH adjuster.

The invention also teaches methods of preparing a suitable formulation for oral administration in a variety of ways, for example in a liquid, a dried mass, a dentifrice, a mouth wash, an oral rinse, a liquid suspension, a topical agent, a powdered food supplement, a paste, a gel, a solid food, a packaged food, a wafer, lozenge, chewing gum and the like. The formulations can also include natural or synthetic flavorings and food-quality coloring agents. Thickening agents can also be added to compositions of the invention such as corn starch, guar gum, carbopol, polyethylene glycol, pluronic F-127 and xanthan gum.

Other formulations will be readily apparent to one skilled in the art. A composition of the invention can include a nutrient supplement component and can include any of a variety of nutritional agents, as are well known, including vitamins, minerals, essential and non-essential amino acids, carbohydrates, lipids, foodstuffs, dietary supplements, and the like.

The invention also teaches the use of liposomal or nanoparticle delivery systems that enhance the stability and efficacy of anti-infective compounds in the compositions. These delivery systems are also useful to deliver a PEGylated and/or fluorinated iron-sequestering glycoprotein apo-ovotransferrin or lactoferrin in combination with chelating agents disodium EDTA and sodium citrate.

DETAILED DESCRIPTION OF THE INVENTION

Definitions

Figure 1:
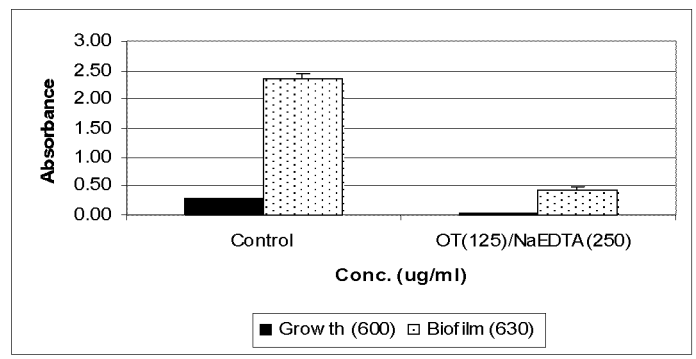
FIG. 1 is a bar graph showing the inhibitory effect of ovotransferrin (OT) and disodium ethylenediaminetetraacetic acid (NaEDTA) combination on dental caries-associated dental plaque forming *Streptococcus mutans* biofilm.
Figure 2:
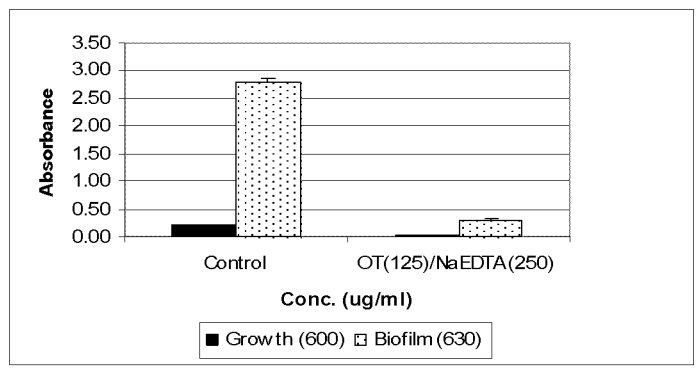
FIG. 2 is a bar graph showing the inhibitory effect of ovotransferrin (OT) and disodium ethylenediaminetetraacetic acid (NaEDTA) combination on dental caries-associated dental plaque forming *Streptococcus sobrinus* biofilm.
Figure 3:
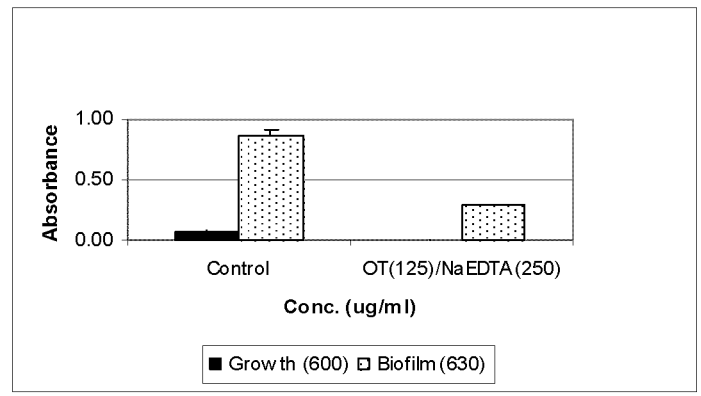
FIG. 3 is a bar graph showing the inhibitory effect of ovotransferrin (OT) and disodium ethylenediaminetetraacetic acid (NaEDTA) combination on dental caries-associated dental plaque forming *Streptococcus oralis* biofilm.
Figure 4:
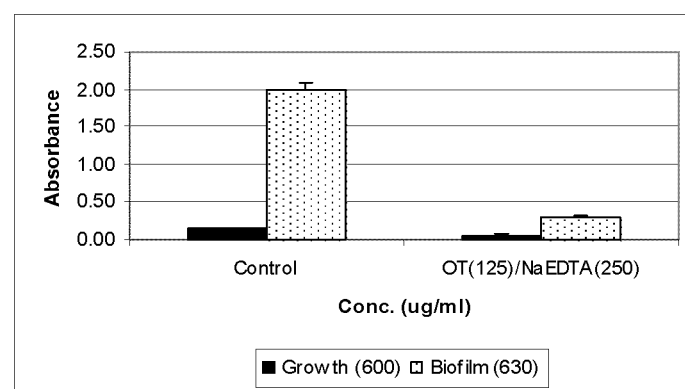
FIG. 4 is a bar graph showing the inhibitory effect of ovotransferrin (OT) and disodium ethylenediaminetetraacetic acid (NaEDTA) combination on dental caries-associated dental plaque forming *Streptococcus sanguis* (*S. sanguinis*) biofilm.

The term "antimicrobial" refers to a compound or a composition that kills or inhibits the growth of microorganisms, including, but not limited to bacteria and yeasts.

The term "biofilm formation" refers to the attachment of microorganisms to surfaces and the subsequent development multiple layers of cells.

The term "dental caries" refers to a localized destruction of tissues of a tooth by acid produced from bacterial degradation of fermentable sugars. The chief etiological agent of dental caries is *S. mutans*. Degradation of fermentable sugars by *S. mutans* on the tooth surface produces an acid that destroys oral tissues, and more particularly, enamel and dentin.

The term "dental plaque" is a general term for the diverse microbial community (predominantly bacteria) found on the tooth surface, embedded in a matrix of polymers of bacterial and salivary origin. Further, "dental plaque-associated *S. mutans*" refers to *S. mutans* that is a component of the dental plaque.

The term "gingivitis" refers to inflammation of gingival tissue without loss of connective tissue.

The term "inhibition" refers to at least a decrease of dental plaque-associated bacterial (e.g., *S. mutans*) growth and biofilm formation.

The term "mammal" for purposes of treatment refers to any animal classified as a mammal, including humans, domestic and farm animals, and zoo, sports or pet animals, such as dogs, horses, cats, cattle, pigs, sheep, etc.

The term "oral diseases" refers to diseases and disorders affecting the oral cavity or associated medical conditions. Oral diseases include, but are not limited to, dental caries; and periodontal diseases (e.g., gingivitis, adult periodontitis, early-onset periodontitis, etc.).

The term "periodontal disease" refers to an inflammatory process of the gingival tissues and/or periodontal membrane of the teeth, resulting in a deep gingival sulcus, possibly producing periodontal pockets and loss of alveolar bone.

The term "periodontitis" refers to inflammation and loss of connective tissue of the supporting or surrounding structure of teeth with loss of attachment.

The term "prophylaxis" or "prevention" refers to at least preventing a condition associated with oral bacteria occurring in a mammal, particularly when the mammal is found to be predisposed to having the condition but has not yet been diagnosed as having it.

The term "subject" refers to a living vertebrate such as mammal (preferably human and pet animals) in need of treatment.

The term "therapeutically effective amount" refers to a quantity of a composition high enough to provide a significant positive modification of the subject's condition(s) to be treated.

A "preventative amount" as used herein includes a prophylactic amount, for example, an amount effective for preventing or protecting against dental caries and related diseases, and symptoms thereof, and amounts effective for alleviating or healing dental caries, related diseases, and symptoms thereof. By administering a peptide suitable for use in methods of the invention concurrently with an antimicrobial, the peptide and/or the antimicrobial may be administered in a dosage amount that is less than the dosage amount required when the antimicrobial is administered as a sole active ingredient. By administering lower dosage amounts of active ingredient, side effects associated therewith could be reduced.

The term "treatment" refers to an intervention performed with the intention of reducing the further development or altering the pathology of an existing disorder. Accordingly, "treatment" refers to therapeutic treatment. Those in need of treatment include those already with the disorder. In regards to dental caries, "treating or treatment" is intended to mean at least the mitigation of a condition associated with *S. mutans* in a subject, such as a mammal, including but not limited to, a human, that is affected at least in part by the condition, and includes, but is not limited to, modulating, inhibiting the condition, and/or alleviating the condition.

The present invention teaches anti-infective compositions offering antimicrobials and anti-biofilm activity, containing combinations of iron-sequestering glycoproteins with other antimicrobial agents, such as, for example, antimicrobials/antibiofilm compounds, chelating agents with surfactants or stabilizing agents.

Novel compositions that combine iron-sequestering glycoproteins together with chelating agents such that lesser quantities of iron-sequestering glycoprotein and/or chelating agents than would normally be necessary for an antimicrobial composition are used to achieve significant bacterial growth and biofilm inhibition. Higher concentrations of these compounds can be used if it is desired for certain applications.

The amount of iron-sequestering glycoprotein to be used in the antimicrobial composition of this invention can be between 25 to 2000 mg/L. The higher end of this stated range might be used to prepare a concentrated product that would be diluted prior to use. For non-concentrated products, the amount of iron-sequestering glycoprotein to be used in this invention is preferably between about 25 to 1000 mg/L. Preferably, the range is between about 25 to 500 mg/L, more preferably between about 25 to 100 mg/L.

The amount of chelating agent to be used should be between about 500 to 4000 mg/L. The higher end of this range might apply if the compositions were formulated as a concentrate. For non-concentrated products, the amount of chelating agent to be used in this invention is preferably between about 500 to 3000 mg/L. Preferably, the range is between about 1000 to 3000 mg/L, more preferably between about 2000 to 3000 mg/L.

Preparation

By one method, if a two-component composition is formed containing a chelating agent and an iron-sequestering glycoprotein, these compounds can be combined in the following manner. With good stirring, a chelating agent can be dissolved in water, followed by an iron-sequestering glycoprotein. It should be noted, however, that the addition order can be reversed.

Additionally, antimicrobials/antimicrobial peptides, antibiotics, antibiofilm compounds, quaternary ammonium compounds and surfactants also may be advantageously combined with iron-sequestering glycoprotein in an antimicrobial composition. A composition of the invention comprises: (a) a small amount of at least one iron-sequestering glycoprotein; (b) a small amount of an antimicrobial peptide or an antibiotic or an antibiofilm compound; and (c) a sparing amount of at least one compound from the group consisting of a stabilizing agent and/or a surfactant, wherein, the amount of each of components (a), (b) and (c) is sufficient to form, in combination, an effective anti-infective composition for prevention and treatment of oral cavity diseases.

The concentration of active components in the compositions may vary as desired or necessary to decrease the amount of time the composition of the invention is used to prevent or treat oral diseases. These variations in active components concentration are easily determined by persons skilled in the art.

Compositions

The present invention includes enhanced oral anti-infective compositions for the prevention or prophylaxis of oral diseases comprising at least one iron-sequestering glycoprotein and one chelating agent.

In an embodiment, an iron-sequestering glycoprotein and a chelating agent containing composition includes an antimicrobial compound. An iron-sequestering glycoprotein and a chelating agent containing composition with an antimicrobial and/antibiofilm compound has an enhanced inhibitory effect on oral bacterial growth and biofilm formation. Furthermore, addition of an antimicrobial compound to a composition containing an iron-sequestering glycoprotein and a chelating agent can make the composition effective against oral pathogens associated with dental caries, gingivitis and periodontitis.

In an embodiment of the invention, an enhanced oral antimicrobial-antibiofilm composition comprises at least one iron-sequestering glycoprotein, one chelating agent and one or more antimicrobial agents comprising benzimidazoles (e.g., lansoprazole and omeprazole), polyols (e.g., xylitol, sorbitol, etc.), polyphenols (e.g., epigallocatechin gallate), antiseptics (e.g., triclosan, chlorhexidine salt, cetylpyridinium chloride, etc.), antibiotics, anti-caries agents, and bacteriocins (e.g., nisin, epidermin, gallidennin, cinnamycin, duramycin, lacticin 481, etc.). Additionally, the oral compositions may comprise ingredients such as citrate (e.g., citric acid, zinc citrate, sodium citrate, potassium citrate, etc.), minerals (e.g., mineral salts such as zinc chloride, zinc gluconate, zinc lactate, zinc citrate, etc.), triterpenoids (e.g., oleanolic acid and ursolic acid) and chitosan In an embodiment, a composition comprises an antibiotic and iron-sequestering glycoprotein and also one chelating agent. Antibiotics are well known. Groups of antibiotics include, but are not limited to, β-lactam inhibitors (e.g., penicillin, ampicillin, amoxicillin, methicillin, etc.), cephalosporins (e.g., cephalothin, cephamycin, etc.), aminoglycosides (e.g., streptomycin, tobramycin, etc.), polyenes (e.g., amphotericin, nystatin, etc.), macrolides (e.g., erythromycin, etc.), tetracyclines (e.g., tetracycline, doxycycline, etc.), nitroimidazole (e.g., metronidazole), quinolones (e.g., nalidixic acid), rifamycins (e.g., rifampin), and sulfonamides (e.g., sulfanilamide), nitroaromatics (e.g., chloramphenicol) and pyridines (e.g., isoniazid).

In an embodiment, a composition comprises a polyphenol, an iron-sequestering glycoprotein and one chelating agent. An example of a polyphenol is epigallocatechin gallate (EGCg). EGCg is a catechin isolated from green tea and has anti-oxidant and immunomodulatory activities (Matsunaga et al., 2002, *Clin. Diagn. Lab. Immunol.* 9: 864-871). Antimicrobial activity of polyphenols such as tannins from thyme, cashew and *eucalyptus* are also advantageous (Cowan, *Clin. Microbiol. Rev.* 12:564-582, 1999)

In an embodiment, a composition comprises a polyol, an iron-sequestering glycoprotein and one chelating agent. Polyols, also known as sugar alcohols, are carbohydrate sugar-free sweeteners. Polyols are derived from carbohydrates with carbonyl groups reduced to a primary or secondary hydroxyl group. Polyols include, but are not limited to, sorbitol, xylitol, mannitol, and maltitol. Polyols are known to limit growth and biofilm formation in oral Streptococci that are associated with dental plaque, a precursor of calculus (tartar) and dental caries.

In an embodiment, a composition comprises a bacteriocin, an iron-sequestering glycoprotein and one chelating agent. Bacteriocins include lantibiotics. *S. mutans* produces bacteriocin antimicrobial molecules called mutacins. Mutacins have been classified into two families: the lantibiotics and the non-antibiotics. Examples of bacteriocins include, but are not limited to, nisin, epidernin, gallidermin, cinnamycin, duramycin, lacticin 481, mutacin I, B-Ny266, and mutacin 1140. See, also, U.S. Pat. Nos. 6,699,970; 6,699,839; 6,475,771; 6,391,285; 6,342,385; 6,218,362; and 5,932,469.

In an embodiment, a composition comprises an antiseptic, an iron-sequestering glycoprotein and one chelating agent. Antiseptics are agents that kill or inhibit the growth of microorganisms on the external surfaces of the body. Antiseptics include, but are not limited to, triclosan, chlorhexidine salt, and cetylpyridinium chloride.

In an embodiment, a composition comprises an antibiofilm compound, an iron-sequestering glycoprotein and a chelating agent. Antibiofilm compounds include, but not limited to, DNase I, Proteinase K, apyrase, cis-2-decenoic acid, alginate lyase, lactoferrin, gallium, and 5-fluorouracil.

In an embodiment, a composition comprises one or more anti-caries agents, an iron-sequestering glycoprotein and one chelating agent. Various anti-caries agents are well known and are included in an embodiment of the present invention. Various anti-caries agents include, but are not limited to benzoic esters, sesquiterpene alcohols (e.g., farnesol, nerolidol, bisabolol, and santalol), halogenated carbanilides, phenolic compounds, aromatic halophenols, resorcinols, catechols, bisphenolic compounds, histidine-rich polypeptides, fluorides (sodium fluoride, stannous fluoride, amine fluorides, monosodiumfluorophosphate, calcium lactate, calcium glycerophosphate, proline-rich proteins, non-immunogenic amino acid segment, and antibodies of *S. mutans*.

In an embodiment, a composition is effective for inhibiting growth and biofilm formation in oral disease associated bacteria. Under appropriate environmental conditions, populations of *S. mutans* and the pH of the surrounding plaque will drop. *S. mutans*, being among the most acid tolerant organisms residing in dental plaque, will increase its numbers in this acidic environment and eventually become a dominant member of the plaque community. This situation eventually leads to dissolution of the tooth enamel, resulting in the development of dental caries. Infections can be modulated using embodiments of the invention.

An embodiment of the invention may also include other pharmaceutically acceptable vehicles, diluents, and additives such as antioxidants, buffers and solutes, which render the formulation isotonic in the intended recipient; and aqueous and non-aqueous sterile suspensions which may include suspending agents and thickening agents.

Oral Formulations

A composition of the invention can be added to a variety of formulations suitable for delivery of the composition to the oral cavity, including, but not limited to, mouthwash solutions, abrasive dentifrice gels, denture washes, nonabrasive dentifrice gels, denture washes or soaks, denture adhesives or cements, chewing gums, candies, soft drinks, and sports drinks. To provide such formulations, a composition of this invention is combined with one or more orally acceptable carriers and/or excipients.

Formulations including, but not limited to, mouthwash solutions, abrasive dentifrice gels, denture washes, nonabrasive dentifrice gels, denture washes or soaks, denture adhesives or cements, chewing gums, candies, soft drinks, sports drinks and other orally acceptable compositions comprising an iron-sequestering glycoprotein and a chelating agent in combination with a benzimidazole, a polyol, a polyphenol, an antiseptic, an antibiotic, a bacteriocin, a citrate, or a triterpenoid or chitosan can be prepared by any known method.

In general, methods of manufacturing oral anti-infective compositions comprise combining an orally acceptable carrier and an effective amount of both iron-sequestering glycoprotein and chelating agent with a benzimidazole, a polyol, a polyphenol, an antiseptic, an antibiotic, a bacteriocin, an anti-caries agent, a citrate, a triterpenoid, or chitosan.

A variety of carriers and excipients can be used to formulate an embodiment of this invention and are well known. Such orally acceptable vehicles include, but are not limited to, water, ethanol, humectants such as polypropylene glycol, glycerol and sorbitol, gelling agents such as cellulose derivatives, polyoxypropylene/polyoxyethylene block copolymers, binding agents such as Gantrez™, pyrophosphates, bisphosphates, thickening agents such as Carbopol™934, gel stabilizers such as silicon dioxides, sweeteners such as sodium saccharin, and other approved flavors, preservatives such as sodium benzoate, potassium sorbate, methyl and ethyl parabens, detergents such as sodium lauryl sulfate, sodium lauryl sarcosinate and approved colors.

Method of Treatment

Another aspect of this invention includes a method for treating dental caries, gingivitis and periodontitis. In general, dental caries and periodontal diseases may be treated by contacting the oral cavity of a subject with an amount of an iron-sequestering glycoprotein and a chelating agent in combination with one or more anti-caries/antimicrobial agents effective to reduce oral bacteria associated with dental caries, gingivitis and periodontitis.

In one embodiment, an iron-sequestering glycoprotein and a chelating agent together is formulated as an orally acceptable medicament as described herein comprising a carrier and an effective amount of composition comprising an iron-sequestering glycoprotein and a chelating agent as active ingredients.

An exemplary dosing regime of an oral composition of this invention is application of a composition to the oral cavity of a subject (animal or human) every time a subject eats a feed or food containing sugar. For example, people generally eat foods containing sugar from one to three times a day. According to this embodiment, a subject would apply a composition of the invention to the oral cavity from one to three times daily soon after consuming a sugar-containing food or beverage as part of a routine oral hygiene program to inhibit or treat dental caries, as a routine to prevent or treat gingivitis, or as a routine to prevent or treat periodontal diseases. For animals or pets, the composition of the invention can be used in drinking water or in feed once a day or in paste to brush the teeth once a day or in biscuits to chew once or twice a day.

In a further embodiment of the invention, an enhanced oral anti-infective composition does not present tooth-staining and toxicity problems. Also, the composition of this invention comprising an iron-sequestering glycoproteins (Ovotransferrin or Lactoferrin) and chelating agents (NaEDTA and Sodium Citrate) have GRAS (Generally Recognized as Safe) status.

The present invention may be better understood with reference to the following examples. These examples are intended to be representative of specific embodiments of the invention, and are not intended as limiting the scope of the invention.

EXAMPLES

Example 1

Inhibitory Effect of Ovotransferrin (OT) and Disodium Ethylenediaminetetraacetic Acid (NaEDTA) Combination on Dental Caries-Associated Biofilms

A 96-well crystal violet staining biofilm assay was used to determine the inhibitory effect of ovotransferrin (OT) and disodium ethylenediaminetetraacetic acid (NaEDTA) combination on dental caries causing bacteria involved in dental plaque (biofilm) formation. Briefly, stock cultures were grown under anaerobic conditions in Todd Hewitt media containing 0.3% Yeast Extract (THYE), and 0.01% hog gastric mucin, pH 7.0. Biofilms were developed in 96-well Costar 3598 microtiter plates (Corning Inc., Corning, N.Y.). Growth of static biofilms was initiated by inoculation of overnight culture at 3.3% into semi-defined minimal (SDM) media containing salts (58 mM $K_2HPO_4$, 15 mM $KH_2PO_4$, 10 mM $(NH_4)_2SO_4$, 35 mM NaCl, and 2 mM $MgSO_4.7H_2O$) vitamins (0.04 mM nicotinic acid, 0.1 mM pyridoxine HCl, 0.01 mM pantothenic acid, 1 µM riboflavin, 0.3 µM thiamine HCl, 0.05 µM d-Biotin), amino acids (4 mM L-glutamic acid, 1 mM L-arginine HCl, 1.3 mM L-cysteine HCl, 0.1 mM L-tryptophan), 0.2% casamino acids, and 20 mM glucose, pH 7.0. Bacteria were grown in the absence (control) or presence of ovotransferrin (OT, 125 µg/ml) and disodium EDTA (NaEDTA, 250 µg/ml) combination. Plates were incubated *S. mutans* UA159, *S. sobrinus* HNG 909S, *S. oralis* NCTC11472 and *S. sanguis* NCTC10904 for 16 h at 37° C. under anaerobic conditions. Biofilm development was measured by crystal violet staining and optical density measurements. The medium containing planktonic cells was discarded, and the biofilm was rinsed once with 200 µl of water per well and air dried overnight. The biofilm cells were stained with 200 µl 0.4% (wt/vol) crystal violet for 15 min. Crystal violet was removed and the wells were rinsed three times each with 200 µl water. Plate was air dried for 15 min, stain in each well was solubilized in 200 µl of 33% acetic acid and absorbance at 630 nm was measured using a microtiter plate reader (Multiskan Ascent, Labsystems, Helsinki, Finland). For each experiment, background staining was corrected by subtracting the crystal violet bound to uninoculated controls. All comparative analyses were conducted by incubating different strains in the same 96-well microtiter plate to minimize variability. The combination of OT (125 µg/ml) and NaEDTA (250 g/ml) had a significant inhibitory effect on biofilms of all four tested *Streptococcus* species (FIG. 1, FIG. 2, FIG. 3 and FIG. 4, respectively) associated with dental plaque resulting in calculus and dental caries.

Example 2

Inhibitory Effect of Ovotransferrin (OT) and Disodium Ethylenediaminetetraacetic Acid (NaEDTA) Combination on Gingivitis-Associated Biofilm

Figure 5A:
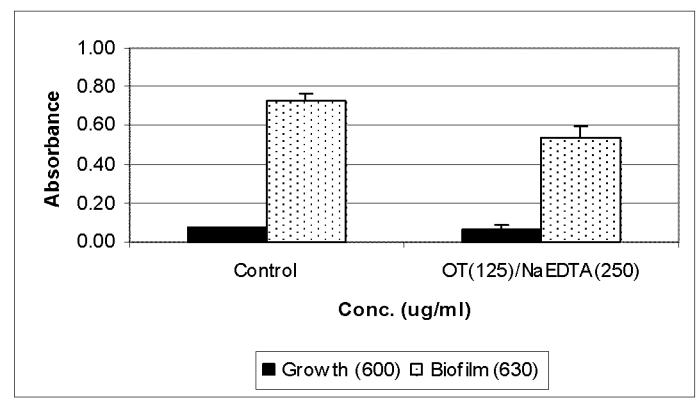
FIG. 5a is a bar graph showing the inhibitory effect of ovotransferrin (OT, 125 μg/ml) and disodium ethylenediaminetetraacetic acid (NaEDTA, 250 μg/ml) combination on gingivitis-associated *Porphyromonas gingivalis* biofilm.
Figure 5B:
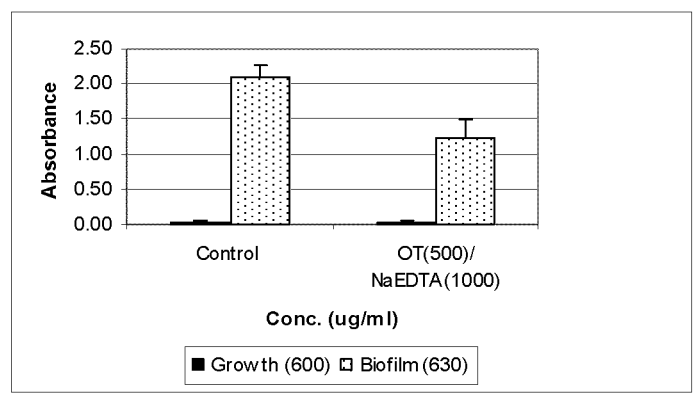
FIG. 5b is a bar graph showing the inhibitory effect of ovotransferrin (OT, 500 μg/ml) and disodium ethylenediaminetetraacetic acid (NaEDTA, 1000 μg/ml) combination on gingivitis-associated *Porphyromonas gingivalis* biofilm.

A 96-well crystal violet staining biofilm assay was used to determine the inhibitory effect of ovotransferrin (OT) and disodium ethylenediaminetetraacetic acid (NaEDTA) combination on gingivitis-associated biofilm formation. Briefly, glycerol stocks were grown on Tryptic Soy Agar plates supplemented with 0.025% menadione (5 mg/ml), 0.1% hemin (1 mg/ml) and 5% sheep's blood, for 48 h under anaerobic conditions. Liquid cultures (25 ml) were grown under anaerobic conditions (24 h) in Todd Hewitt media supplemented with 0.1% hemin (1 mg/ml) and 0.025% menadione (5 mg/ml). Biofilms were developed in 96-well Costar 3598 microtiter plates (Corning Inc., Corning, N.Y.). Growth of *Porphyromonas gingivalis* W50 static biofilms was initiated by inoculation of overnight culture at 1:10 dilution in a modified salt base media containing (10 mM $Na_2H_2PO_4$, 10 mM KCl, 2 mM $C_6H_8O_7$, 1.25 mM $MgCl_2$, 20 µM $CaCl_2$, 0.1 µM $Na_2MoO_4$, 25 µM $ZnCl_2$, 50 µM $MnCl_2$, 5 µM $CuCl_2$, 10 µM $CoCl_2$, 5 µM $H_3BO_3$, adjusted to pH 7.0). Added to this base is 3% Bovine Serum Albumin, 20 mM α-ketoglutarate and 1% tryptone, this is filter sterilized and supplemented with 0.1% hemin (1 mg/ml) and 0.025% menadione (5 mg/ml). Bacteria were grown in the absence (control) or presence of ovotransferrin (OT, 125 µg/ml & 500 µg/ml) and Sodium EDTA (NaEDTA, 250 µg/ml & 1000 µg/ml) combination. Plates were incubated for 48 h at 37° C. under anaerobic conditions. Biofilm development was measured by crystal violet staining and optical density measurements. The medium containing planktonic cells was discarded, and the biofilm was rinsed twice with 200 µl of water per well and air dried for 1 h. The biofilm cells were stained with 200 µl 0.4% (wt/vol) crystal violet for 15 min. Crystal violet was removed and the wells were rinsed twice with 200 µl water. Plate was air dried for 15 min followed by solubilization in 200 µl of 33% acetic acid and absorbance at 630 nm was measured using a microtiter plate reader (Multiskan Ascent, Labsystems, Helsinki, Finland). For each experiment, background staining was corrected by subtracting the crystal violet bound to uninoculated controls. All comparative analyses were conducted by incubating all agents in the same 96-well microtiter plate to minimize variability. [Note: all plastic ware and media were pre-incubated anaerobically for a minimum of 48 h prior to experiment]. The combinations of OT (125 µg/ml & 500 µg/ml) and NaEDTA (250 µg/ml & 1000 µg/ml) had an appreciable inhibitory effect on biofilm of *P. gingivalis* (FIGS. 5a and 5b) associated with gingivitis.

Example 3

Inhibitory Effect of Ovotransferrin (OT) and Disodium Ethylenediaminetetraacetic Acid (NaEDTA) Combination on Periodontitis-Associated Biofilm

Figure 6:
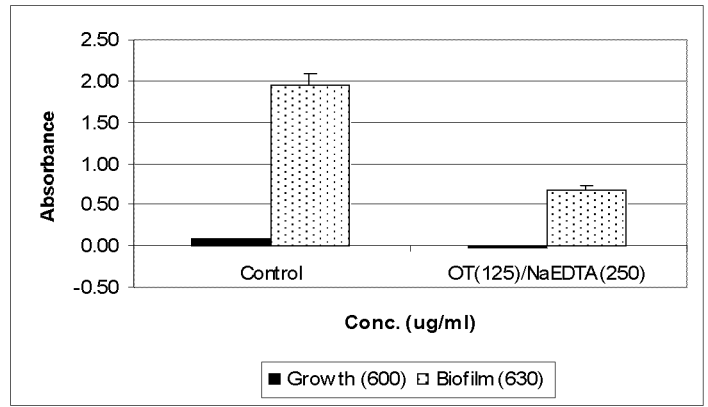
FIG. 6 is a bar graph showing the inhibitory effect of ovotransferrin (OT, 125 μg/ml) and disodium ethylenediaminetetraacetic acid (NaEDTA, 250 μg/ml) combination on periodontitis-associated *Aggregatibacter actinomycetemcomitans* biofilm.

A 96-well crystal violet staining biofilm assay was used to determine the inhibitory effect of ovotransferrin (OT) and disodium ethylenediaminetetraacetic acid (NaEDTA) combination on periodontitis-associated biofilm formation. Briefly, glycerol stocks were grown on Tryptic Soy Agar plates supplemented with 5% sodium bicarbonate for 48 h under anaerobic conditions. Ten colonies of *Aggregatibacter actinomycetemcomitans* UT32 were removed from these plates and transferred to 200 µl of fresh broth [Tryptic Soy broth (30 g/L), Yeast extract (6 g/L), Dextrose (8 g/L)]. Vortex for 10 s, transfer the 200 µl to 2 ml of fresh broth and vortex for 15 s. The inocula is passed through a 5 µM PVDF syringe filter (Millex-SV Cat. No SLSVO25LS). Biofilms were developed in 96-well Costar 3598 microtiter plates (Corning Inc., Corning, N.Y.). Growth of static biofilms was initiated by inoculation of a 1:10 dilution using the inocula in fresh broth. Bacteria were grown in the absence (control) or presence of ovotransferrin (OT, 125 µg/ml) and Sodium EDTA (NaEDTA, 250 µg/ml) combination. Plates were incubated for 48 h at 37° C. under anaerobic conditions. Biofilm development was measured by crystal violet staining and optical density measurements. The medium containing planktonic cells was discarded, and the biofilm was rinsed once with 200 µl of water per well immediately followed by staining with 200 µl 0.4% (wt/vol) crystal violet for 1 min. Crystal violet was removed and the wells were rinsed three times each with 200 µl water. Plate was air dried, stain in each well was solubilized in 200 µl of 33% acetic acid and absorbance at 630 nm was measured using a microtiter plate reader (Multiskan Ascent, Labsystems, Helsinki, Finland). For each experiment, background staining was corrected by subtracting the crystal violet bound to uninoculated controls. All comparative analyses were conducted by incubating all agents in the same 96-well microtiter plate to minimize variability. The combination of OT (125 µg/ml) and NaEDTA (250 µg/ml) had a significant inhibitory effect on biofilm of *A. actinomycetemcomitans* (FIG. 6) associated with periodontitis.

Example 4

Inhibitory Effect of Ovotransferrin (OT) and Disodium EDTA (NaEDTA) Combination on Oral Cavity Diseases Associated Bacteria as Determined by the Minimum Inhibitory Concentration (MIC) Assay The MICs of ovotransferrin and disodium EDTA combination was determined for six organisms including *Streptococcus mutans* (associated with dental plaque and caries), *S. oralis* (associated with dental plaque and caries), *Porphyromonas gingivalis* (associated with gingivitis), *Aggregatibacter actinomycetemcomitans* (associated with periodontitis), *Pseudomonas aeruginosa* (associated with hospital infections) and *Burkholderia multivorans* (associated with lung infections) were determined by using a broth microdilution assay in 96-well microtiter plate assay. Briefly, bacterial strains were grown overnight at 37° C. under anaerobic or aerobic conditions in either THYE media for *Streptococcus* spp. Todd Hewitt broth supplemented with hemin and menadione for *P. gingivalis*, a Tryptic Soy/Yeast Extract broth supplemented with sodium bicarbonate for *A. actinomycetemcomitans* and Luria broth for *P. aeruginosa* and *B. multivorans* then diluted to $10^5$ cfu/mL. A 100 mL aliquot of bacterial suspension was added to each well. Aliquots (100 mL) of the combination were then added to the first column of wells of the microtitre plate. The content of the microtiter plate wells was mixed with a multipipettor and 2-fold serial dilutions were performed to achieve the desired concentrations of the combination. Plates were incubated at 37° C. for 24 h-48 h under anaerobic conditions and read at 600 nm using a microtiter plate reader (Multiskan Ascent, Labsystems, Helsinki, Finland). The MIC was assessed as the lowest antimicrobial concentration that completely inhibited growth. The MIC values were validated post OD assessment by plating each concentration. The highest concentrations tested for MIC was 4000 µg/ml (OT)/8000 µg/ml (NaEDTA). While the MICs of OT/NaEDTA combination for *S. mutans, S. oralis, P. gingivalis* and *A. actinomycetemcomitans* varied from 250 µg/ml (OT)/500 µg/ml (NaEDTA) to 1000 µg/ml (OT)/2000 µg/ml (NaEDTA), the combination did not have any effect on *P. aeruginosa* and *B. multivorans* even at a concentration as high as 4000 µg/ml (OT)/8000 µg/ml (NaEDTA), (Table 1). Thus, the test results demonstrate the selective efficacy of OT and NaEDTA combination against bacteria associated with oral diseases such as dental caries, gingivitis and periodontitis.

TABLE 1

Inhibitory effect of ovotransferrin (OT) and disodium EDTA (NaEDTA) combination on oral disease associated bacteria as determined by the minimum inhibitory concentration (MIC) assay.

| Organism | MIC value of combination OT/NaEDTA (µg/ml) |
|---|---|
| *P. gingivalis* W50 | 250/500 |
| *A. actinomycetemcomitans* UT 32 | 250/500 |
| *S. oralis* NCTC 11472 | 500/1000 |
| *S. mutans* UA 159 | 1000/2000 |
| *P. aeruginosa* KBI-9 | Not effective |
| *B. multivorans* C5393 | Not effective |

Example 5

Method of Preparation of PEGylated Ovotransferrin or Lactoferrin 100 mg of ovotransferrin or Lactoferrin is taken in a 250 ml glass bottle. A buffer containing 100 mM sodium phosphate buffer (pH 5.0) with 20 mM sodium cyanoborohydride and with/without 5% sorbitol is added to the reaction mixture. The methoxy-polyethylene glycol-propionaldehyde (mPEG-aldehyde) of 20 kDa is added to the above stirred solution of the protein. The mPEG-aldehyde is then transferred to the bottle containing protein solution. The protein concentration is maintained at 5 mg/ml. The reaction mixture is then stirred at 2-8° C. overnight. The reaction mixture is quenched by the addition of 40 mM sodium acetate buffer (pH 4.0) with and without 5% sorbitol in the buffer (volume made to five times the reaction volume). The crude reaction mixture is purified by size exclusion chromatography and ion exchange resin and characterized by MALDI mass spectroscopy.

Example 6

Method of Preparation of Fluorinated Ovotransferrin and Lactoferrin

The iron-sequestering glycoproteins such as ovotransferrin and lactoferrin are fluorinated by replacing a few proline or leucine residues with fluoroproline or hexafluoroleucine, respectively. The IPTG inducible vector expressing target protein, i.e. ovotransferrin or lactoferrin with terminal 6×His tag is transferred to *E. coli* expression cell line. Expression vectors devoid of the repressor gene $lacI^q$ are co-transformed with pRE4 encoding $lacI^q$. The expression cell line selected is auxotrophic for the amino acid to be incorporated in to the recombinant protein. Pro-auxotrophic and Leu-auxotrophic *E. coli* strain JM83, and JW5807-2 are used for incorporation of fluoroproline, and hexafluoroleucine, respectively. For incorporation of the selected amino acid analogues, the expression cell line is grown overnight at 37° C. with shaking in 50 ml M9 minimum medium supplemented with auxotrophic amino acid (0.05 mM), and appropriate antibiotics to maintain the expression plasmid. The overnight culture is used to inoculate 500 ml M9 minimal media supplemented with autotrophic amino acid (0.035 mM) and antibiotics. The cells are grown until the auxotrophic amino acid is completely depleted, and then supplemented with fluorinated analogue of auxotrophic amino acid (1 mM) and IPTG (1 mM) for induction of recombinant protein synthesis. The cells are further cultivated at 37° C. with shaking for 12-18 hrs, and harvested by centrifugation. The cells are resuspended in 100 mM Na-phosphate buffer, containing 50 µg/ml lysozyme, 1 mM PMSF and 0.001% Igepal, sonicated, stored on ice for 30 min. Then the lysate is supplemented with RNase (10 µg/ml) and DNase (5 µg/ml), incubated at room temperature for 30 min, and clarified by centrifugation. The cleared lysate is passed through a Ni-Agarose column, washed with 100 Na-Phosphate buffer, and the fluorinated recombinant protein is eluted with 0-100 mM imidazole gradient in 100 mM Na-Phosphate buffer. Eluted fractions containing target protein is pooled and dialyzed against water, and then lyophilized.

Example 7

Method of Preparation of Ovotransferrin and Lactoferrin Nanoparticles 100 mg of Poly D, L-lactide-co-glycolide (PLGA) and 100 mg of ovotransferrin or lactoferrin are dissolved in 6 ml acetone. This solution is added drop wise to 20 ml solution of 0.15% SDS while stirring. The mixture is left stirring for 1 hour and centrifuged at 10,000 rpm for 20 min to pellet the nanoparticles. The liquid was discarded and the pellet is washed 3 times, each time by re-suspending the pellet in 25 ml water followed by the centrifugation at 10,000 rpm for 20 min. Finally, the pellet is air dried in the fume hood and stored at 4° C.

Example 8

Method of Preparation of (i) "Liposomal Ovotransferrin and Disodium Ethylenediaminetetraacetic Acid (NaEDTA) Formulation" and (iii) "Liposomal Lactoferrin, Disodium Ethylenediaminetetraacetic Acid (NaEDTA) and Sodium Citrate (S. Cit)"

Multilamellar liposomes are prepared according to the formula of Novaczek, et al. (1991 Aquatic Toxicology, 21:103-118). A 1:2:7 µM mixture of cholesterol, stearylamine and phosphatidylcholine is used to encapsulate an aqueous solution of ovotransferrin and NaEDTA. The lipid mixture is prepared in chloroform and dried under a fume hood onto the walls of a 25 mm diameter glass test tube. Ovotransferrin-NaEDTA solution is then added, and mixture is vortexed until the lipid film is no longer visible. Resulting liposomes are ultracentrifuged and washed three times to remove free ovotransferrin and NaEDTA.

Example 9

Figure 7A:
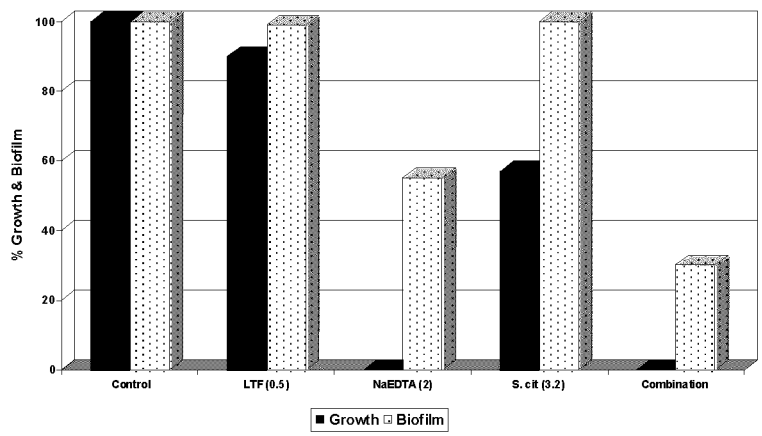
FIG. 7a is a bar graph showing the inhibitory effect of lactoferrin (LTF, 0.5 mg/ml) and disodium ethylenediaminetetraacetic acid (NaEDTA, 2 mg/ml) and sodium citrate (S. cit, 3.2 mg/ml) alone and in combination on dental caries-associated dental plaque forming *Streptococcus mutans* growth and biofilm formation.
Figure 7B:
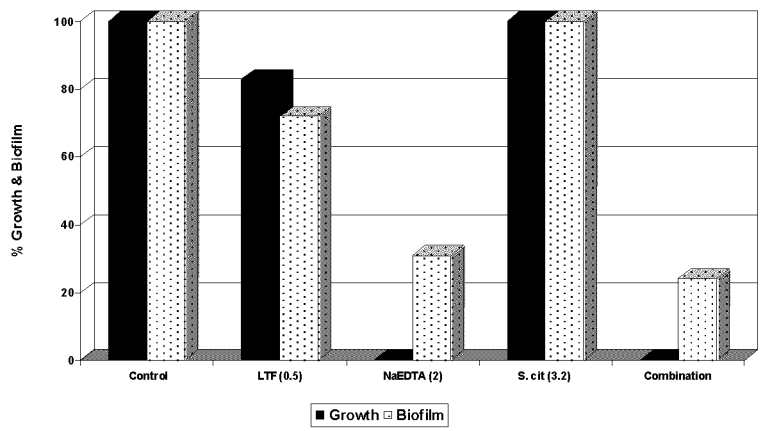
FIG. 7b is a bar graph showing the inhibitory effect of lactoferrin (LTF, 0.5 mg/ml) and disodium ethylenediaminetetraacetic acid (NaEDTA, 2 mg/ml) and sodium citrate (S. cit, 3.2 mg/ml) alone and in combination on dental caries-associated dental plaque forming *Streptococcus sanguis* (*S. sanguinis*) growth and biofilm formation.

Inhibitory Effect of Lactoferrin (LTF), Disodium Ethylenediaminetetraacetic Acid (NaEDTA) and Sodium Citrate (S. Cit) Alone and in Combination on Dental Caries-Associated Biofilms A 96-well crystal violet staining biofilm assay was used to determine the inhibitory effect of lactoferrin (LTF), disodium ethylenediaminetetraacetic acid (NaEDTA) and sodium citrate (S. cit) alone and in combination on dental caries causing bacteria involved in dental plaque (biofilm) formation. Briefly, stock cultures of S. mutans UA159 and S. sanguis (S. sanguinis) NCTC10904 were grown under anaerobic conditions in Todd Hewitt media containing 0.3% Yeast Extract (THYE), and 0.01% hog gastric mucin, pH 7.0. Biofilms were developed in 96-well Costar 3598 microtiter plates (Corning Inc., Corning, N.Y.). Growth of static biofilms was initiated by inoculation of overnight culture at 3.3% into semi-defined minimal (SDM) media containing salts (58 mM $K_2HPO_4$, 15 mM $KH_2PO_4$, 10 mM $(NH_4)_2SO_4$, 35 mM NaCl, and 2 mM $MgSO_4.7H_2O$) vitamins (0.04 mM nicotinic acid, 0.1 mM pyridoxine HCl, 0.01 mM pantothenic acid, 1 µM riboflavin, 0.3 µM thiamine HCl, 0.05 µM d-Biotin), amino acids (4 mM L-glutamic acid, 1 mM L-arginine HCl, 1.3 mM L-cysteine HCl, 0.1 mM L-tryptophan), 0.2% casamino acids, and 20 mM glucose, pH 7.0. Bacteria were grown in the absence (control) or presence of lactoferrin (LTF, 500 µg/ml), disodium EDTA (NaEDTA, 2.5 mg/ml) and sodium citrate (S. cit, 3.2 mg/ml) alone and in combination. Plates were incubated for 16 h at 37° C. under anaerobic conditions. Biofilm development was measured by crystal violet staining and optical density measurements. The medium containing planktonic cells was discarded, and the biofilm was rinsed once with 200 µl of water per well and air dried overnight. The biofilm cells were stained with 200 µl 0.4% (wt/vol) crystal violet for 15 min. Crystal violet was removed and the wells were rinsed three times each with 200 µl water. Plate was air dried for 15 min, stain in each well was solubilized in 200 µl of 33% acetic acid and absorbance at 630 nm was measured using a microtiter plate reader (Multiskan Ascent, Labsystems, Helsinki, Finland). For each experiment, background staining was corrected by subtracting the crystal violet bound to uninoculated controls. All comparative analyses were conducted by incubating different strains in the same 96-well microtiter plate to minimize variability. The combination of LTF (0.5 mg/ml), NaEDTA (2.5 mg/ml) and S. cit (3.2 mg/ml) had a significant inhibitory effect on biofilms when tested on *Streptococcus mutans* and *S. sanguis* (*S. sanguinis*) (FIGS. 7a & 7b, respectively) associated with dental plaque resulting in calculus and dental caries.

Example 10

Figure 8:
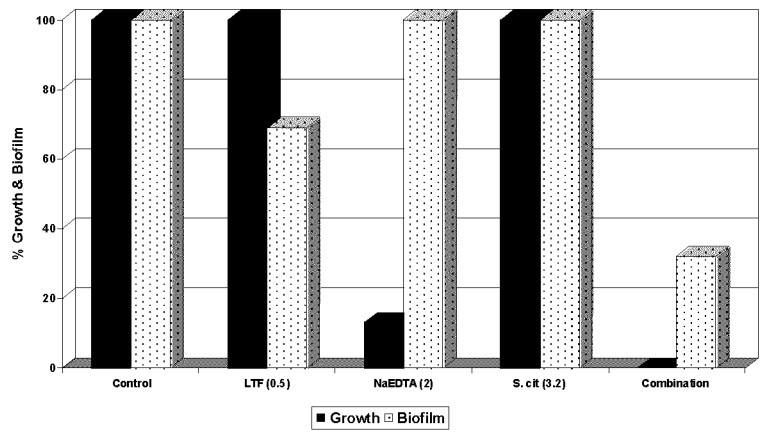
FIG. 8 is a bar graph showing the inhibitory effect of lactoferrin (LTF, 0.5 mg/ml) and disodium ethylenediaminetetraacetic acid (NaEDTA, 2 mg/ml) and sodium citrate (S. cit, 3.2 mg/ml) alone and in combination on periodontitis-associated *Aggregatibacter actinomycetemcomitans* growth and biofilm formation.

Inhibitory Effect of Lactoferrin (LTF), Disodium Ethylenediaminetetraacetic Acid (NaEDTA) and Sodium Citrate (S. Cit) Alone and in Combination on Periodontitis-Associated Biofilm A 96-well crystal violet staining biofilm assay was used to determine the inhibitory effect of lactoferrin (LTF), disodium ethylenediaminetetraacetic acid (NaEDTA) and sodium citrate (S. cit) alone and in combination on periodontitis-associated biofilm formation. Briefly, glycerol stocks were grown on Tryptic Soy Agar plates supplemented with 5% sodium bicarbonate for 48 h under anaerobic conditions. Ten colonies of *Aggregatibacter actinomycetemcomitans* UT32 were removed from these plates and transferred to 200 µl of fresh broth [Tryptic Soy broth (30 g/L), Yeast extract (6 g/L), Dextrose (8 g/L)]. Vortex for 10 s, transfer the 200 µl to 2 ml of fresh broth and vortex for 15 s. The inocula is passed through a 5 µM PVDF syringe filter (Millex-SV Cat. No SLSVO25LS). Biofilms were developed in 96-well Costar 3598 microtiter plates (Corning Inc., Corning, N.Y.). Growth of static biofilms was initiated by inoculation of a 1:10 dilution using the inocula in fresh broth. Bacteria were grown in the absence (control) or presence of lactoferrin (LTF, 0.5 mg/ml) and disodium EDTA (NaEDTA, 2.0 mg/ml) Sodium citrate (S. cit, 3.2 mg/ml) alone or in combination. Plates were incubated for 48 h at 37° C. under anaerobic conditions. Biofilm development was measured by crystal violet staining and optical density measurements. The medium containing planktonic cells was discarded, and the biofilm was rinsed once with 200 µl of water per well immediately followed by staining with 200 µl 0.4% (wt/vol) crystal violet for 1 min. Crystal violet was removed and the wells were rinsed three times each with 200 µl water. Plate was air dried, stain in each well was solubilized in 200 µl of 33% acetic acid and absorbance at 630 nm was measured using a microtiter plate reader (Multiskan Ascent, Labsystems, Helsinki, Finland). For each experiment, background staining was corrected by subtracting the crystal violet bound to uninoculated controls. All comparative analyses were conducted by incubating all agents in the same 96-well microtiter plate to minimize variability. The combination of LTF (0.5 mg/ml), NaEDTA (2.0 mg/ml) and S. cit (3.2 mg/ml) had a significant inhibitory effect on biofilm of *A. actinomycetemcomitans* (FIG. 8) associated with periodontitis.

Example 11

Inhibitory Effect of Lactoferrin (LTF), Disodium Ethylenediaminetetraacitic Acid (NaEDTA) and Sodium Citrate (S. Cit) Alone, in Pairs and in Combination on Oral Cavity Diseases Associated Bacteria as Determined by the Minimum Bactericidal Concentration (MBC) Assay The MBCs of lactoferrin (LTF), disodium EDTA (NaEDTA) and sodium citrate (S. cit) each alone and in pairs (LTF & NaEDTA, LTF & S. cit & NaEDTA & S. cit) and all three (LTF/NaEDTA/S.cit) in combination was determined for two organisms including *Streptococcus sanguis* (dog, associated with dental plaque), and *P. cangingivalis* (dog, associated with canine gingivitis) were determined by using a broth micro-dilution assay in 96-well microtiter plate assay followed by plating to confirm cell death. Briefly, bacterial strains were grown overnight at 37° C. under anaerobic or aerobic conditions in either THYE media for *Streptococcus* spp. Todd Hewitt broth supplemented with hemin and menadione for *P. cangingivalis* then diluted to $10^5$ cfu/mL. A 100 mL aliquot of bacterial suspension was added to each well. Aliquots (100 mL) of the combination were then added to the first column of wells of the microtitre plate. The content of the microtiter plate wells was mixed with a multipipettor and 2-fold serial dilutions were performed to achieve the desired concentrations of the combination. Plates were incubated at 37° C. for 24 h-48 h under anaerobic conditions and read at 600 nm using a microtiter plate reader (Multiskan Ascent, Labsystems, Helsinki, Finland). The MBC was assessed as the lowest antimicrobial concentration that completely inhibited growth. The MBC values were validated post OD assessment by plating each concentration. The highest concentrations tested for MBC was 20 mg/ml (LTF), 8 mg/ml (NaEDTA) and 112 mg/ml (S. cit).

The MBCs of LTF showed that LTF used alone up to a concentration of 20 mg/ml was not able to completely inhibit *S. sanguis* (*S. sanguinis*) and *P. cangingivalis* (first column of Table 2). In the case of NaEDTA alone up to a concentration of 8.0 mg/ml was not able to completely inhibit *P. cangingivalis*, but was able to inhibit completely the growth of *S. sanguis* (*S. sanguinis*) at 2.0 mg/ml (second column of Table 2). In the case of S. cit alone a concentration of 112 and 28 mg/ml was able to inhibit completely *S. sanguis* (*S. sanguinis*) and *P. cangingivalis*, respectively (third column of Table 2). In the case of the three 2 compound combinations (LTF & NaEDTA; LTF & S. cit; and NaEDTA & S. cit)]for *S. sanguis* (*S. sanguinis*) and *P. cangingivalis* the concentration of LTF with either NaEDTA or S. cit decreased substantially to inhibit growth completely (fourth and fifth column of Table 2). In the case of NaEDTA & S. cit combination *S. sanguis* (*S. sanguinis*) and *P. cangingivalis* were completely inhibited with the 1.0/1.7 concentration (sixth column of Table 2). In the case of all three compounds used in combination *S. sanguis* (*S. sanguinis*) showed substantial decrease in the concentration of LTF and NaEDTA to see complete inhibition. In the case of *P. cangingivalis* a substantial decrease in LTF, NaEDTA and S. cit to see complete inhibition (seventh column in Table 2). Thus, the test results demonstrate the efficacy of LTF/NaEDTA/S. cit combination against bacteria associated with oral conditions and diseases such as dental plaque, gingivitis and periodontitis.

TABLE 2

Inhibitory effect of lactoferrin (LTF), disodium EDTA (NaEDTA) and sodium citrate (S. cit) alone and in pairs (LTF & NaEDTA, LTF & S. cit, NaEDTA & S.cit) and then in a combination (LTF/NaEDTA/S. cit) on oral disease associated bacteria as determined by the minimum bactericidal concentration (MBC) assay.

| Organism | MBC LTF (mg/ml) | MBC NaEDTA (mg/ml) | MBC S. cit (mg/ml) | MBC LTF & NaEDTA (mg/ml) | MBC LTF & S. cit (mg/ml) | MBC NaEDTA & S. cit (mg/ml) | MBC LTF/ NaEDTA/ S. cit (mg/ml) |
|---|---|---|---|---|---|---|---|
| *S. sanguis* (*S. sang-uinis*) | >20.0 | 2.0 | 112 | 1.0/1.0 | 0.250/1.7 | 1.0/1.7 | 0.0078/2/1.7 |
| *P. cangingivalis* | >20.0 | >8.0 | 28 | 0.0078/1.0 | 0.0078/1.7 | 1.0/1.7 | 0.0078/2/1.7 |

Example 12

Figure 9:
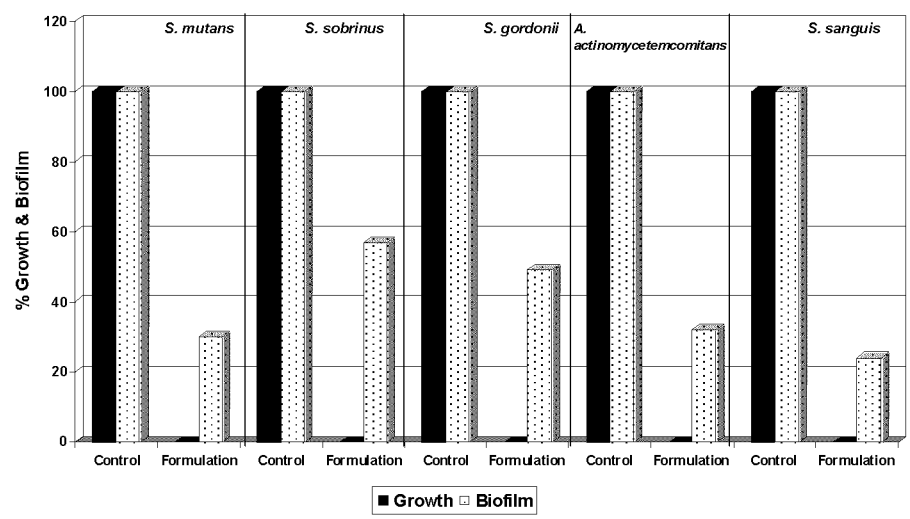
FIG. 9 is a bar graph showing the inhibitory effect of lactoferrin (LTF, 0.5 mg/ml) and disodium ethylenediaminetetraacetic acid (NaEDTA, 2 mg/ml) and sodium citrate (S. cit, 3.2 mg/ml) formulation on dental caries-associated dental plaque forming periodontitis-associated *Streptococcus mutans, S. sobrinus, S. gordonii, S. sanguis* (*S. sanguinis*) and periodontitis-associated *Aggregatibacter actinomycetemcomitans* growth and biofilm.

Inhibitory Effect of Lactoferrin (LTF), Disodium Ethylenediaminetetraacetic Acid (NaEDTA) and Sodium Citrate (S. Cit) Formulation on Dental Caries and Periodontitis-Associated Biofilms A 96-well crystal violet staining biofilm assay was used to determine the inhibitory effect of lactoferrin (LTF), disodium ethylenediaminetetraacetic acid (NaEDTA) and sodium citrate (S. cit) formulation on dental caries causing and dental plaque (biofilm) forming bacteria. Also tested was a periodontitis-associated bacterium. *Streptococcus* strains *S. mutans* UA159, *S. sobrinus* HNG 909S, *S. gordonii* and SK120 *S. sanguis* (*S. sanguinis*) NCTC10904 were grown as per Example #10. *A. actinomycetemcomitans* was grown as per Example #11. The formulation of LTF (0.5 mg/ml), NaEDTA (2.0 mg/ml) and S. cit (3.2 mg/ml) had a significant inhibitory effect on biofilms of all four tested *Streptococcus* species associated with dental plaque resulting in calculus and dental caries and *A. actinomycetemcomitans* associated with periodontal disease (FIG. 9).

Example 13

Figure 10A:
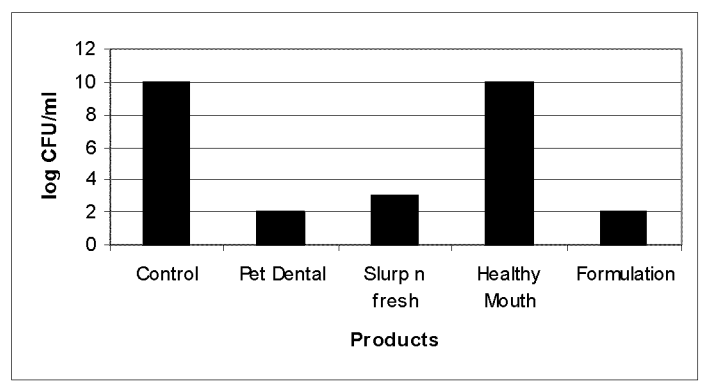
FIG. 10a is a bar graph showing the inhibitory effect of Formulation containing lactoferrin (LTF, 0.5 mg/ml) and disodium ethylenediaminetetraacetic acid (NaEDTA, 2 mg/ml) and sodium citrate (S. cit, 3.2 mg/ml) in comparison with that of commercial pet oral care products (Pet Dental, Slurp n fresh and Healthy mouth) on dental caries-associated dental plaque forming *Streptococcus mutans* biofilm.
Figure 10B:
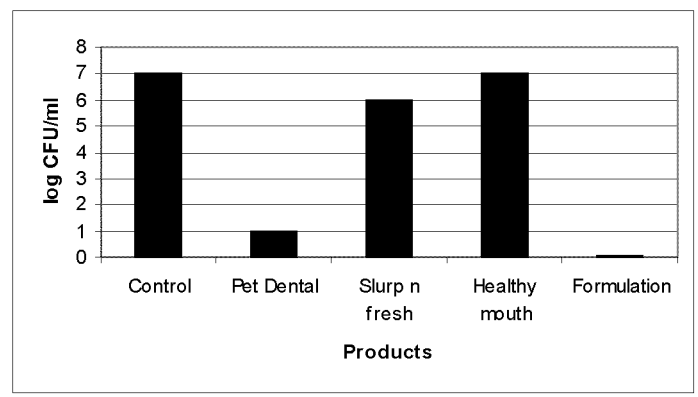
FIG. 10b is a bar graph showing the inhibitory effect of formulation containing lactoferrin (LTF, 0.5 mg/ml) and disodium ethylenediaminetetraacetic acid (NaEDTA, 2 mg/ml) and sodium citrate (S. cit, 3.2 mg/ml) in comparison with that of commercial pet oral care products (Pet Dental, Slurp n fresh and Healthy mouth) on dental caries-associated dental plaque forming *Streptococcus sanguis* biofilm.
Figure 10C:
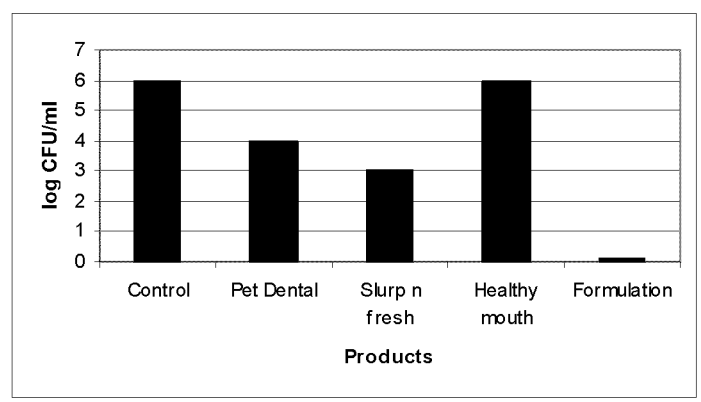
FIG. 10c is a bar graph showing the inhibitory effect of formulation containing lactoferrin (LTF, 0.5 mg/ml) and disodium ethylenediaminetetraacetic acid (NaEDTA, 2 mg/ml) and sodium citrate (S. cit, 3.2 mg/ml) in comparison with that of commercial pet oral care products (Pet Dental, Slurp n fresh and Healthy mouth) on periodontitis-associated *Aggregatibacter actinomycetemcomitans* biofilm.

Comparison of Inhibitory Effect of Lactoferrin (LTF), Disodium Ethylenediaminetetraacetic Acid (NaEDTA) and Sodium Citrate (S. Cit) Formulation with that of Commercial Companion Animal Oral Care Products on Biofilms A 12-well polystyrene microtiter plate biofilm assay was used to determine the inhibitory effect of lactoferrin (LTF), disodium ethylenediaminetetraacetic acid (NaEDTA) and sodium citrate (S. cit) Formulation on oral disease bacteria. Briefly, *S. mutans* UA159, *S. sanguis* (*S. sanguinis*) NCTC10904 and *A. actinomycetemcomitans* biofilms were developed on 12-well polystyrene microtiter plate to provide a rapid and simple method for assaying biofilm-embedded live oral bacteria. A 4× diluted THYE medium supplemented with final concentration of 0.01% hog gastric mucin was used as biofilm medium (BM) for *S. mutans* and *S. sanguis* (*S. sanguinis*). A specific BM [Tryptic Soy broth (30 g/L), Yeast extract (6 g/L), Dextrose (8 g/L)] was used for *A. actinomycetemcomitans*. Biofilm was initiated by inoculating 20 µl of cell suspension into each well containing 2 ml of BM and twelve wells were set up: two for control and two for each treatment (Pet Dental, Slurp n fresh, Healthy mouth and the Formulation) and two for blank. Cultures were incubated at 37° C. for 20 hours under an anaerobic condition, fluid medium was removed. The wells were rinsed once with 10 mM PBS buffer (pH 7.2) and biofilm-embedded cells were collected in two ml PBS buffer by gentle sonication for 15 seconds, diluted then spread on THYE plates and incubated at 37° C. under an anaerobic conditions. Biofilm-embedded viable cells were quantified by colony forming unit (CFU) counts after 48 hours of incubation. The Formulation of LTF (0.5 mg/ml), NaEDTA (2.0 mg/ml) and S. cit (3.2 mg/ml) performed better than the other companion animal oral care products on the market (FIGS. 10a, 10b & 10c).

Example 14

Figure 11:
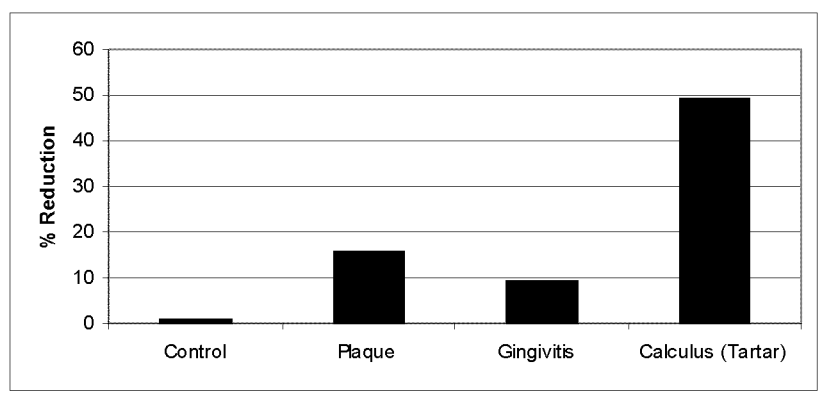
FIG. 11 is a bar graph showing the effect of drinking water additive formulation containing lactoferrin (LTF, 0.5 mg/ml) and disodium ethylenediaminetetraacetic acid (NaEDTA, 2 mg/ml) and sodium citrate (S. cit, 3.2 mg/ml) in reducing plaque, gingivitis and calculus (tartar) in Beagle dogs compared to untreated control Beagle dogs.
Figure 12A:
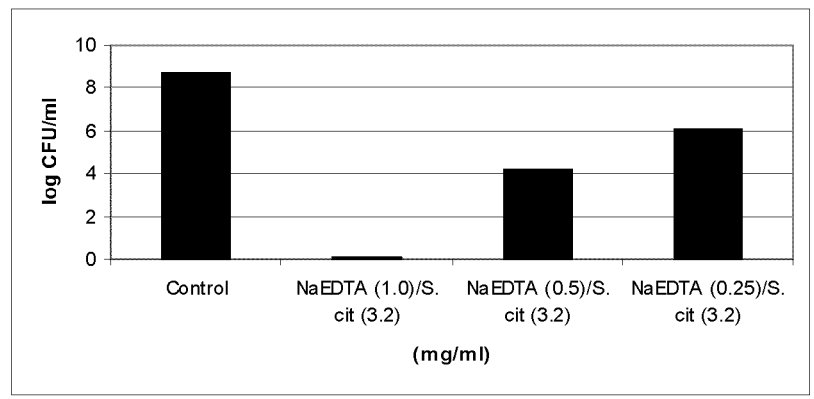
FIG. 12a is a bar graph showing the inhibitory effect of varying concentrations of disodium ethylenediaminetetraacetic acid (NaEDTA, 1.0, 0.5 and 0.25 mg/ml) and sodium citrate (S. cit, 3.2 mg/ml) combinations on dental caries-associated dental plaque forming *Streptococcus mutans* biofilm.
Figure 12B:
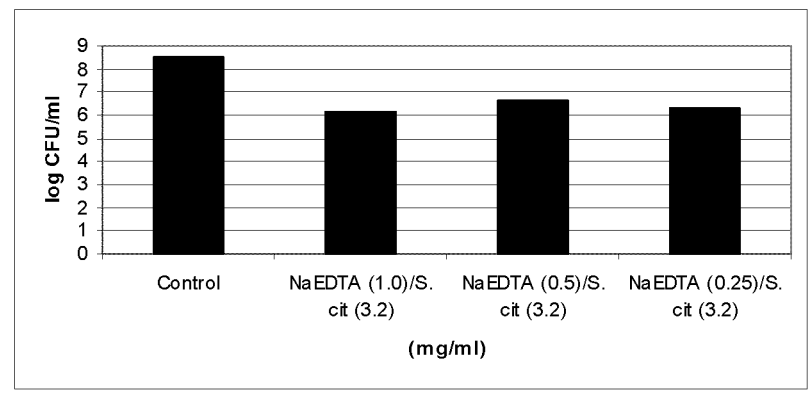
FIG. 12b is a bar graph showing the inhibitory effect of varying concentrations of disodium ethylenediaminetetraacetic acid (NaEDTA, 1.0, 0.5 and 0.25 mg/ml) and sodium citrate (S. cit, 3.2 mg/ml) combinations on dental caries-associated dental plaque forming *Streptococcus gordonii* biofilm.
Figure 12C:
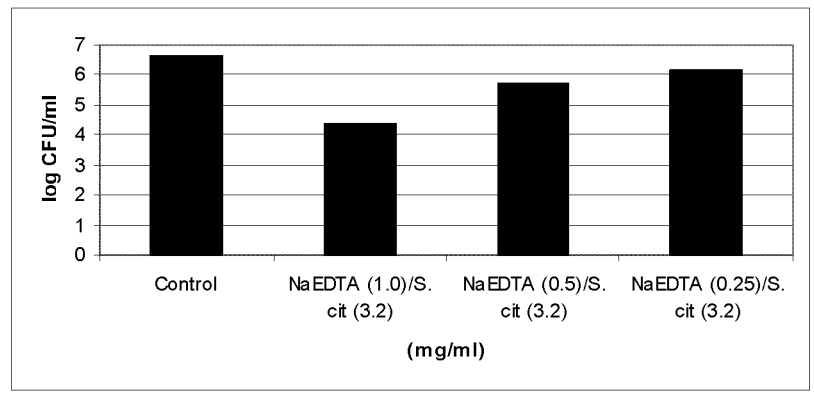
FIG. 12c is a bar graph showing the inhibitory effect of varying concentrations of disodium ethylenediaminetetraacetic acid (NaEDTA, 1.0, 0.5 and 0.25 mg/ml) and sodium citrate (S. cit, 3.2 mg/ml) combinations on dental caries-associated dental plaque forming *Streptococcus sanguis* (*S. sanguinis*) biofilm.
Figure 12D:
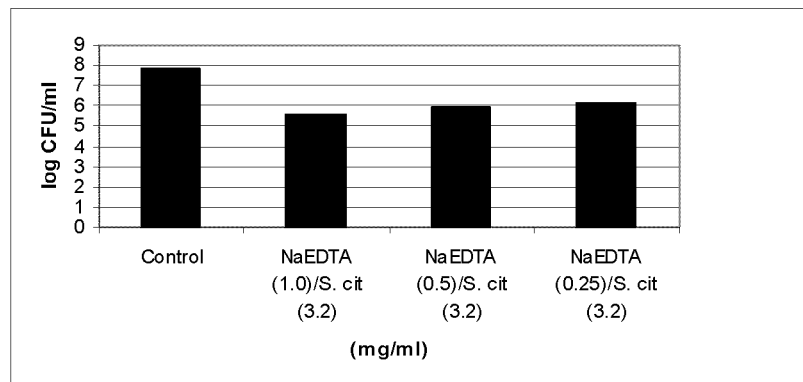
FIG. 12d is a bar graph showing the inhibitory effect of varying concentrations of disodium ethylenediaminetetraacetic acid (NaEDTA, 1.0, 0.5 and 0.25 mg/ml) and sodium citrate (S. cit, 3.2 mg/ml) combinations on periodontitis-associated *Aggregatibacter actinomycetemcomitans* biofilm.

In Vivo Efficacy of Oral Formulation Containing Lactoferrin (LTF), Disodium EDTA (NaEDTA) and Sodium Citrate (S. Cit) as Active Ingredients The objective of the in vivo pilot efficacy study using the VOHC (Veterinary Oral Health Council, PA, USA) recommended test protocol for dogs was to demonstrate the effect of LTF-NaEDTA-S.cit formulation in reducing dental plaque, calculus (tartar) and gingivitis. An equal number of dogs (adult Beagles) were recruited for the control and test groups. All dogs in the study were of similar size and had no missing teeth. The dogs were anesthetized and a dental cleaning was performed by a veterinarian on each dog. Before the dogs were entered into the study and after dental cleaning, dogs were scored at a level of 0 (meaning completely plaque and tartar free) for both upper and lower jaws. The Formulation containing LTF (0.5 mg/ml), NaEDTA (2 mg/ml) and S. cit (3.2 mg/ml) as active ingredients was added to regular drinking water in the test group and regular drinking water was given to the control group. For the duration of the trial all dogs (treatment and control) were fed a control diet (kibble, fed dry). The study monitored food and water consumption, and also body weight change in dogs on LTF-NaEDTA-S.cit formulation vs. the control. The teeth scored in each dog were: Upper Jaw (13, C, P3, P4, MI), Lower Jaw (C, P3, P4, MI). Duration of the study was 14 days. The pilot study results showed appreciable reduction in dental plaque, calculus/tartar and gingivitis (FIG. 11). Furthermore, no difference in food or water consumption and in body weight was observed, suggesting that all dogs were in good health. This pilot study demonstrates the efficacy of LTF-NaEDTA-S.cit formulation against bacteria associated with dental plaque and periodontal disease in dogs.

Example 15

Inhibitory Effects of Formulations Containing Varying Concentrations of Disodium Ethylenediaminetetraacetic Acid (NaEDTA) and a Fixed Concentration of Sodium Citrate (S. Cit) on Oral Cavity Diseases Associated Biofilms A 12-well polystyrene microtiter plate biofilm assay was used to determine the inhibitory effect of formulations containing varying concentrations of NaEDTA (1, 0.5 and 0.25 mg/ml) and fixed concentration of S. cit. (3.2 mg/ml) on oral disease bacteria. Briefly, *S. mutans* UA159, *S. gordonii*, *S. sanguis* (*S. sanguinis*) NCTC10904 and *A. actinomycetemcomitans* biofilms were developed on 12-well polystyrene microtiter plate to provide a rapid and simple method for assaying biofilm-embedded live oral bacteria. A 4× diluted THYE medium supplemented with final concentration of 0.01% hog gastric mucin was used as biofilm medium (BM) for *S. mutans, S. gordonii* and *S. sanguis* (*S. sanguinis*). A specific BM [Tryptic Soy broth (30 g/L), Yeast extract (6 g/L), Dextrose (8 g/L)] was used for *A. actinomycetemcomitans*. Biofilm was initiated by inoculating 20 µl of cell suspension into each well containing 2 ml of BM and twelve wells were set up: three for control and three for each treatment and three for blank. Cultures were incubated at 37° C. for 20 hours under an anaerobic condition, fluid medium was removed. The wells were rinsed once with 10 mM PBS buffer (pH 7.2) and biofilm-embedded cells were collected in two ml PBS buffer by gentle sonication for 15 seconds, diluted and then spread on THYE plates and incubated at 37° C. under anaerobic conditions. Biofilm-embedded viable cells were quantified by colony forming unit (CFU) counts after 48 hours of incubation. The three test formulations containing varying concentrations of NaEDTA and a fixed concentration of S. cit showed different degrees of biofilm reduction in test organisms (FIGS. 12a, 12b 12c & 12d).

Example 16

Figure 13A:
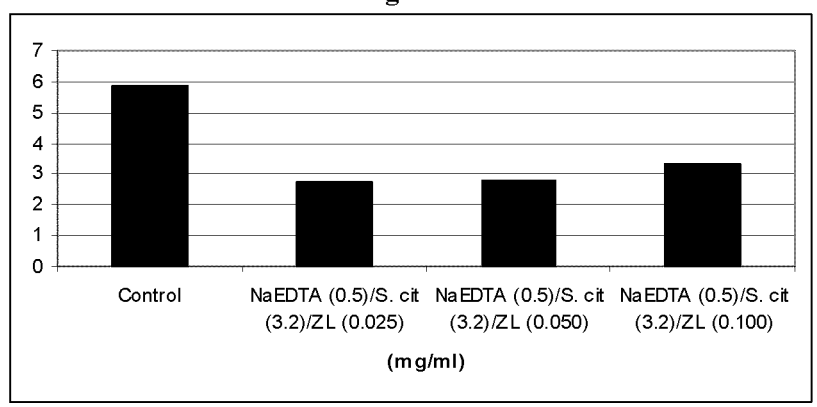
FIG. 13a is a bar graph showing the inhibitory effects of formulations containing fixed concentrations of disodium ethylenediaminetetraacetic acid (NaEDTA, 0.5 mg/ml) and sodium citrate (S. cit, 3.2 mg/ml) and varying concentrations of zinc lactate (ZL, 0.10, 0.05, 0.025 mg/ml) on dental caries-associated dental plaque forming *Streptococcus sanguis* (*S. sanguinis*) biofilm
Figure 13B:
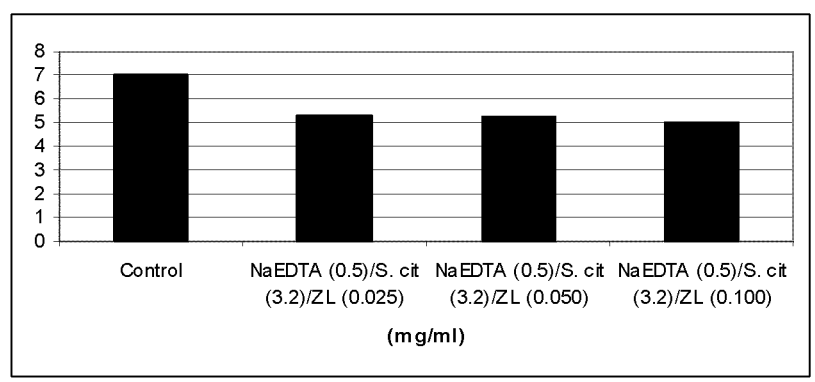
FIG. 13b is a bar graph showing the inhibitory effects of formulations containing fixed concentrations of disodium ethylenediaminetetraacetic acid (NaEDTA, 0.50 mg/ml) and sodium citrate (S. cit, 3.2 mg/ml) and varying concentrations of zinc lactate (ZL, 0.10, 0.05, 0.025 mg/ml) on periodontitis-associated *Aggregatibacter actinomycetemcomitans* biofilm.
Figure 14A:
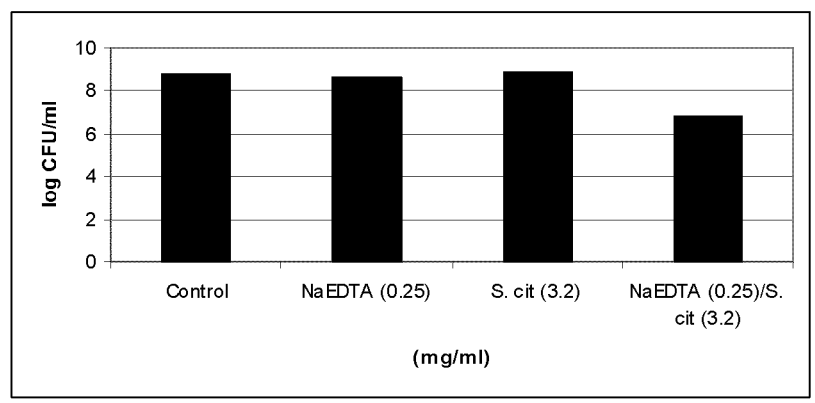
FIG. 14a is a bar graph showing the synergistic inhibitory effect of disodium ethylenediaminetetraacetic acid (NaEDTA, 0.25 mg/ml) and sodium citrate (S. cit 3.2 mg/ml) combination compared to the effect of individual compounds on *Streptococcus mutans* biofilm.
Figure 14B:
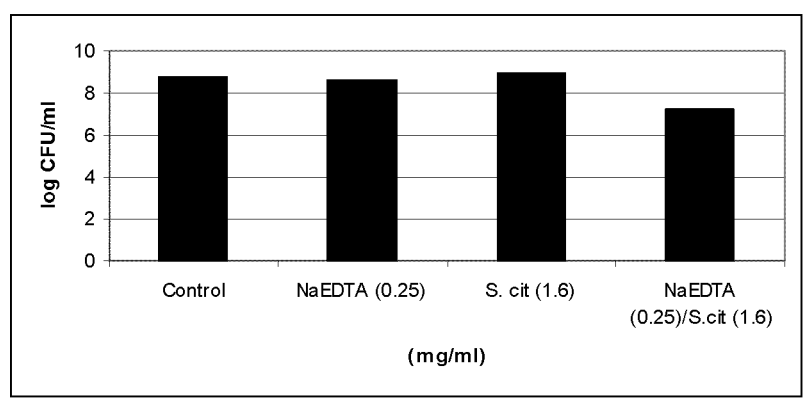
FIG. 14b is a bar graph showing the synergistic inhibitory effect of disodium ethylenediaminetetraacetic acid (NaEDTA, 0.25 mg/ml) and sodium citrate (S. cit 1.6 mg/ml) combination compared to the effect of individual compounds on *Streptococcus mutans* biofilm.
Figure 14C:
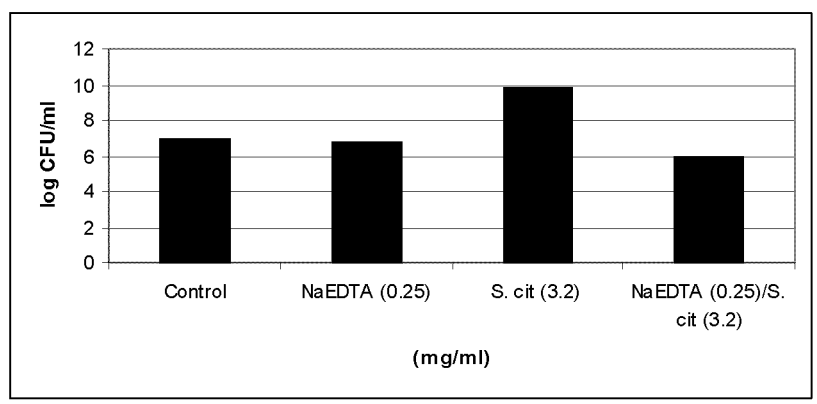
FIG. 14c is a bar graph showing the synergistic inhibitory effect of disodium ethylenediaminetetraacetic acid (NaEDTA, 0.25 mg/ml) and sodium citrate (S. cit 3.2 mg/ml) combination compared to the effect of individual compounds on *Aggregatibacter actinomycetemcomitans* biofilm.
Figure 14D:
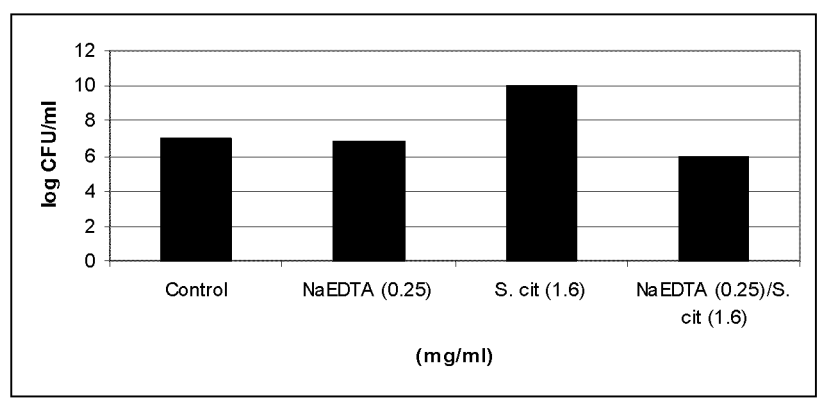
FIG. 14d is a bar graph showing the synergistic inhibitory effect of disodium ethylenediaminetetraacetic acid (NaEDTA, 0.25 mg/ml) and sodium citrate (S. cit 1.6 mg/ml) combination compared to the effect of individual compounds on *Aggregatibacter actinomycetemcomitans* biofilm.

Inhibitory Effects of Formulations Containing Fixed Concentrations of Disodium Ethylenediaminetetraacetic Acid (NaEDTA) and Sodium Citrate (S. Cit) and Varying Concentrations of Zinc Lactate (ZL) on Oral Cavity Diseases Associated Biofilms A 12-well polystyrene microtiter plate biofilm assay was used to determine the inhibitory effect of formulations containing fixed concentrations of NaEDTA (0.5 mg/ml) and S. cit. (3.2 mg/ml) and varying concentrations of ZL (0.025, 0.050 and 0.1 mg/ml) on oral disease bacteria. Briefly, *S. sanguis* (*S. sanguinis*) NCTC10904 and *A. actinomycetemcomitans* biofilms were developed on 12-well polystyrene microtiter plate to provide a rapid and simple method for assaying biofilm-embedded live oral bacteria. A 4× diluted THYE medium supplemented with final concentration of 0.01% hog gastric mucin was used as biofilm medium (BM) for *S. sanguis* (*S. sanguinis*). A specific BM [Tryptic Soy broth (30 g/L), Yeast extract (6 g/L), Dextrose (8 g/L)] was used for *A. actinomycetemcomitans*. Biofilm was initiated by inoculating 20 µl of cell suspension into each well containing 2 ml of BM and twelve wells were set up: three for control and three for each treatment and three for blank. Cultures were incubated at 37° C. for 20 hours under an anaerobic condition, fluid medium was removed. The wells were rinsed once with 10 mM PBS buffer (pH 7.2) and biofilm-embedded cells were collected in two ml PBS buffer by gentle sonication for 15 seconds, diluted and then spread on THYE plates and incubated at 37° C. under anaerobic conditions. Biofilm-embedded viable cells were quantified by colony forming unit (CFU) counts after 48 hours of incubation. The three test formulations containing varying concentrations of ZL and fixed concentrations of NaEDTA and S. cit showed slightly more or less similar biofilm reduction in test organisms (FIGS. 13*a* & 13*b*).

Example 17

Synergistic Inhibitory Effect of Disodium Ethylenediaminetetraacetic Acid (NaEDTA) and Sodium Citrate (S. Cit) Combinations Compared to the Effect of Individual Compounds on Oral Cavity Diseases Associated Biofilms A 12-well polystyrene microtiter plate biofilm assay was used to determine the synergistic inhibitory effect of NaEDTA (0.025 and 0.5 mg/ml) and S. cit. (1.6 and 3.2 mg/ml) alone and in combinations on oral disease bacteria. Briefly, *S. mutans* and *A. actinomycetemcomitans* biofilms were developed on 12-well polystyrene microtiter plate to provide a rapid and simple method for assaying biofilm-embedded live oral bacteria. A 4× diluted THYE medium supplemented with final concentration of 0.01% hog gastric mucin was used as biofilm medium (BM) for *S. sanguis* (*S. sanguinis*). A specific BM [Tryptic Soy broth (30 g/L)], Yeast extract (6 g/L), Dextrose (8 g/L)] was used for *A. actinomycetemcomitans*. Biofilm was initiated by inoculating 20 µl of cell suspension into each well containing 2 ml of BM and twelve wells were set up: three for control and three for each treatment and three for blank. Cultures were incubated at 37° C. for 20 hours under an anaerobic condition, fluid medium was removed. The wells were rinsed once with 10 mM PBS buffer (pH 7.2) and biofilm-embedded cells were collected in two ml PBS buffer by gentle sonication for 15 seconds, diluted and then spread on THYE plates and incubated at 37° C. under anaerobic conditions. Biofilm-embedded viable cells were quantified by colony forming unit (CFU) counts after 48 hours of incubation. Unexpectedly, NaEDTA and S. cit in combinations at lower concentrations showed more reduction in *S. mutans* and *A. actinomycetemcomitans* biofilms compared to individual compounds, indicating a strong synergy between two compounds (FIGS. 14*a*, 14*b*, 14*c* & 14*d*).

We claim:

1. A composition for reducing bacterial biofilm formation in the oral cavity, the composition consisting essentially of:

(a) ethylenediaminetetraacetic acid (EDTA) between about 250 mg/L and about 1000 mg/L of the composition;

(b) a citrate selected from one or more of sodium citrate and potassium citrate, wherein the citrate is at a concentration between about 1600 mg/L and about 3200 mg/L; and (c) a zinc salt selected from the group consisting of zinc lactate, zinc gluconate, zinc citrate, and zinc chloride, wherein said zinc salt is at a concentration of 25 mg/L to 100 mg/L, prepared as one or more of a mouthwash, an oral rinse, a spray, an abrasive dentifrice gel, a dentifrice, a denture wash, a denture soak, a topical agent, a denture adhesive, a denture cement, a lozenge, and a pet chew biscuit.

2. The composition of claim 1, wherein the bacteria is selected from the group consisting of *Streptococcus mutans, Streptococcus sobrinus, Streptococcus sanguis (sanguinis), Streptococcus gordonii, Streptococcus oralis, Streptococcus mitis, Actinomyces odontolyticus, Actinomyces viscosus, Aggregatibacter actinomycetemcomitans, Porphyromonas gingivalis, Prevotella intermedia, Bacteroides forsythus, Treponema denticola, Fusobacterium nucleatum, Campylobacter rectus, Eikenella corrodens, Veillonella spp., Micromonas micros, Porphyromonas cangingivalis, Haemophilus actinomycetemcomitans Actinomyces spp., Bacillus spp., Mycobacterium spp., Fusobacterium spp., Streptococcus spp., Staphylococcus aureus, Streptococcus pyogenes, Streptococcus agalectiae, Proteus mirabilis, Klebsiella pneumoniae, E. coli, Acinetobacter spp., Enterococcus spp., Prevotella spp., Porphyromonas spp., Clostridium spp., Stenotrophomonas maltophilia* and *P. cangingivalis.*

3. The composition of claim 1, further comprising one or more ingredients selected from the group consisting of: water, a buffer, a stabilizing agent, a binding agent, a gelling agent, a desensitizing agent, a teeth whitening agent, an antiplaque deposition aide, a surfactant, a herbal, a vitamin, a mineral, a pH adjuster, a flavor, and a color.

4. The composition of claim 1, wherein the EDTA is disodium EDTA.

5. The composition of claim 4, wherein the disodium EDTA is present at about 500 mg/L.

6. The composition as claimed in claim 1, wherein the composition comprises a liposomal or nanoparticle delivery system.

7. The composition of claim 1, wherein said EDTA is in the form of a disodium or tetrasodium salt.

8. A composition for reducing bacterial biofilm formation in the oral cavity, the composition consisting essentially of: sodium citrate in a concentration of about 3.2 mg/ml, disodium EDTA in a concentration of about 0.5 mg/ml, and a zinc salt selected from the group consisting of zinc lactate, zinc gluconate, zinc citrate, and zinc chloride, said zinc salt in a concentration of about 0.025 to 0.100 mg/ml, prepared as one or more of a mouthwash, an oral rinse, a spray, an abrasive dentifrice gel, a dentifrice, a denture wash, a denture soak, a topical agent, a denture adhesive, a denture cement, a lozenge, and a pet chew biscuit.

9. The composition of claim 8, further comprising one or more selected from the group consisting of: water, a buffer, a stabilizing agent, a binding agent, a gelling agent, a desensitizing agent, a teeth whitening agent, an antiplaque deposition aide, a surfactant, a herbal, a vitamin, a mineral, a pH adjuster, a flavor, and a color.

10. A composition for reducing bacterial biofilm formation in the oral cavity, the composition comprising an antimicrobial agent consisting essentially of:
(a) ethylenediaminetetraacetic acid (EDTA) between about 250 mg/L and about 1000 mg/L of the composition; and
(b) a citrate selected from one or more of sodium citrate and potassium citrate, wherein the citrate is at a concentration between about 1600 mg/L and about 3200 mg/L,
prepared as one or more of a mouthwash, an oral rinse, a spray, an abrasive dentifrice gel, a dentifrice, a denture wash, a denture soak, a topical agent, a denture adhesive, a denture cement, a lozenge, and a pet chew biscuit.

11. A method of reducing bacterial biofilm formation in the oral cavity comprising orally administering the composition of claim 1, wherein the bacteria biofilm is caused by at least one of the bacteria selected from the group consisting of *Streptococcus mutans, Steptococcus sobrinus, Streptococcus sanguis (sanguinis), Streptococcus gordonii, Streptococcus oralis, Streptococcus mitis, Actinomyces odontolyticus, Actinomyces viscosus, Aggregatibacter actinomycetemcomitans. Porphyromonas gingivalis, Prevotella intermedia, Bacteroides forsythus, Treponema denticola, Fusobacterium nucleatum, Campylobacter rectus, Eikenella corrodens, Veillonella* spp., *Micromonas micros, Porphyromonas cangingivalis, Haemophilus actinomycetemcomitans Actinomyces* spp., *Bacillus* spp., *Mycobacterium* spp., *Fusobacterium* spp., *Streptococcus* spp., *Staphylococcus aureus, Streptococcus pyogenes, Streptococcus agalectiae, Proteus mirabilis, Klebsiella pneumoniae, E. coli, Acinetobacter* spp., *Enterococcus* spp., *Prevotella* spp., *Porphyromonas* spp., *Clostridium* spp., *Stenotrophomonas maltophilia* and *P. cangingivalis*.

* * * * *